(12) United States Patent
Zhou et al.

(10) Patent No.: US 9,949,479 B2
(45) Date of Patent: Apr. 24, 2018

(54) METCONAZOLE-CONTAINING PESTICIDE COMPOSITION FOR PREVENTING AND CONTROLLING FUSARIUM HEAD BLIGHT AND APPLICATION THEREOF

(71) Applicant: NANJING AGRICULTURAL UNIVERSITY, Nanjing (CN)

(72) Inventors: Mingguo Zhou, Nanjing (CN); Yabing Duan, Nanjing (CN); Jianxin Wang, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 0 days.

(21) Appl. No.: 15/550,494

(22) PCT Filed: May 11, 2016

(86) PCT No.: PCT/CN2016/081655
§ 371 (c)(1),
(2) Date: Aug. 11, 2017

(87) PCT Pub. No.: WO2017/084249
PCT Pub. Date: May 26, 2017

(65) Prior Publication Data
US 2018/0049436 A1    Feb. 22, 2018

(30) Foreign Application Priority Data
Nov. 19, 2015   (CN) .......................... 2015 1 0801884

(51) Int. Cl.
*A01N 43/16*   (2006.01)
*A01N 43/653*   (2006.01)

(52) U.S. Cl.
CPC ........... *A01N 43/16* (2013.01); *A01N 43/653* (2013.01); *A01N 2300/00* (2013.01)

(58) Field of Classification Search
None
See application file for complete search history.

(56) References Cited

FOREIGN PATENT DOCUMENTS

CN        102057914 A   *   5/2011   ........... A01N 43/653

* cited by examiner

*Primary Examiner* — Brian J Davis
(74) *Attorney, Agent, or Firm* — CBM Patent Consulting, LLC

(57) ABSTRACT

It relates to a pesticide composition for preventing and controlling *fusarium* head blight, which contains 1 to 150 parts by weight of jinggangmycin and 1 to 20 parts by weight of metconazole per mu. The pesticide composition of the present invention has an obvious synergistic effect when used for preventing and controlling *fusarium* head blight, and can remarkably enhance the effect of preventing and controlling head blight, increasing the ability of the human being in preventing and controlling head blight of triticeae crops.

11 Claims, No Drawings

METCONAZOLE-CONTAINING PESTICIDE COMPOSITION FOR PREVENTING AND CONTROLLING FUSARIUM HEAD BLIGHT AND APPLICATION THEREOF

This application is the U.S. national phase of International Application No. PCT/CN2016/081655 filed on 11 May 2016 which designated the U.S. and claims priority to Chinese Application Nos. CN201510801884.5 filed on 19 Nov. 2015, the entire contents of each of which are hereby incorporated by reference.

FIELD OF THE INVENTION

The invention belongs to the technical field of pesticides. More specifically, the present invention relates to a pesticide composition for preventing and controlling *fusarium* head blight, and further relates to an agricultural fungicide for preventing and controlling *fusarium* head blight.

BACKGROUND OF THE INVENTION

Wheat and barley are the most important cultivated grain crops in the world as well as one of the main food crops in China. Grain crops are often confronted with the threat of fungal diseases such as head blight, powdery mildew, sheath blight, rust and leaf blight. These diseases may occur in worldwide grain growing regions, severely affecting the yield and quality of agricultural grain products. Especially, *fusarium* head blight caused by fusaria not only can result in devastating yield loss, but also can produce toxins, such as deoxynivalenol (DON) and zearalenon in infected grains, consequently, the quality of food, such as fermented food and brewed liquors, is severely affected, and the health of the human being and animals are harmed.

The deoxynivalenol toxin includes DON, 3A DON and 15A DON toxins, which have acute and chronic toxicity to human being and animals. As the DON toxin has stable chemical properties and won't be decomposed when heated, the DON toxin widely exists in head blight fungus-infected barley and wheat, processed food thereof and animal products fed with grains infected by head blight fungi. It has been known that the main symptoms of human and animal poisoning caused by the DON toxin include nausea, emesis, dizziness, drowsiness, headache, numb hands and feet, general weakness and decrease in immunity, the fluctuation of breath, pulse, body temperature and blood pressure, bleeding, miscarriage and even death can be seen in severe cases, and the DON toxin can cause human Kaschin-Beck disease (KBD) and has obvious embryotoxicity and teratogenic and carcinogenic effects. Since the DON toxin has severe harm to human health. In the joint conference on food additives and contaminants held in Geneva in October, 1973, the United Nations world food and agriculture organization (FAO) and the world health organization (WHO) decided to include *fusarium* toxins into the fifth topic among sixteen topics given priority in research, and many countries have also always considered the prevention and control of head blight as an important research topic.

Moreover, many international organizations and national health organizations have laid down corresponding laws and regulations to strictly limit DON toxin content in food. FAO provides that the content of DON in food must be less than 1 mg/kg, and WHO provides that the content of the DON toxin in food and feed cannot respectively exceed the standards of 1 mg/kg and 5 mg/kg. The European Union food safety standard requires that the content of the DON toxin cannot exceed 0.75 mg/kg in edible kernels and cannot exceed 0.5 mg/kg in bread and other foods. The national standard established by the Ministry of Health in China provides that the content of the DON toxin in edible wheat flour and corn cannot exceed 1 mg/kg.

*Fusarium* head blight is an ascomycete disease, including bud rot, seedling blight and ear rot/ear blight, caused by a variety of fusaria (*Fusarium* spp.). It includes nearly twenty varieties of pathogens, such as *fusarium graminearum* (*F. graminearum*), *fusarium asiaticum* (*F. asiaticum*), *fusarium culmorum* (*F. culmorum*), *fusarium avenaceum* (*F. avenaceum*), *fusarium moniliforme* (*F. moniliforme*) and *fusarium nivale* (*F. nivale*). *Fusarium* head blight in most of the regions in China is caused by the mixed population of *fusarium graminearum* (*F. graminearum*) and *fusarium asiaticum* (*F. asiaticum*), *fusarium asiaticum* is mainly in the southern wheat region, and *fusarium graminearum* is mainly in the northern wheat region.

As no grain crop varieties or gene resources which are immune or highly resistant to fusaria have been found as yet, using fungicides has become the only effective *fusarium* head blight prevention and control technology. For almost a century, people have been carrying out a great deal of work to research and develop fungicides for triticeae fungal diseases, and have developed inorganic fungicides, organosulfureous fungicides and aromatic hydrocarbon protective fungicides in succession, especially selective fungicides developed after 1960s, such as benzimidazole fungicides, ergosterol biosynthesis inhibitors, cytochrome b inhibitors and succinodehydrogenase inhibitors, so that the epidemic harm of a lot of important triticeae crop diseases, such as grain crop smut, powdery mildew, rust, leaf blight and eyespot, has been effectively controlled. However, as the deoxynivalenol (DON) toxin produced by fusaria (*Fusarium* spp.) has the function of a pathogenic factor, the resistance to a variety of fungicides is enhanced, and as a result, the prevention and control effect of the majority of fungicides on *fusarium* head blight is not very ideal. Therefore, how to effectively control grain crop head blight is a current significant social demand in guaranteeing grain safety and food safety.

The DON toxin contamination level of diseased grain depends on the quantity of pathogenic fungi infecting the grain and the toxin biosynthesis capability of thalli. Aimed at the situation that the prevention and control effect of today's domestic and foreign main fungicides for preventing and controlling *fusarium* head blight is not ideal and that DON toxin contamination often exceeds edible safety standards, the present invention studies and discovers two types of β-tubulin ($β_1$ and $β_2$-) receptors for benzimidazole fungicides existing in fusaria and a genetic negative regulation mechanism for fungicide resistance and fungicide sensitivity for the first time, and discovers that the 240th amino acid phenylalanine composing the $β_2$-tubulin receptor is a main cause of fungicide sensitivity decrease and that the point mutation of the 167th amino acid will cause carbendazim to lose the prevention and control effect and greatly enhance the DON toxin synthesis capability, mycelial colonization speed and pathogenecity of thalli, decreasing the prevention control effect of fungicides; in addition, the study also discovers an ergosterol biosynthesis inhibitor (EBI) receptor of fusaria, i.e. cytochrome $P_{450}$ monooxygenase, or fungicide sensitivity or fungicide resistance to EBI can be decreased by the overexpression or point mutation of encoding genes. Therefore, although some fungicides show very high activity in the lab, high dosages are needed when the fungicides are applied in fields, for example, 40 g to 50 g (600-750 g a.i./hm²) of benzimidazole fungicide with above active ingredients or 15 g to 20 g (225-300 g a.i./hm²) of EBI with above active ingredients need to be used per mu to obtain about 70 percent of *fusarium* head blight control effect.

As these selective fungicides with single acting mechanisms are used in a large amount for a long term, fungicide resistance will appear in pathogenic fungus populations in the nature, and the effect in use will decrease year by year. After nearly thirty years of fungicide resistance monitoring, the inventor discovers that fusaria which have developed fungicide resistance to benzimidazole fungicides, such as carbendazim, have formed a dominant population in Eastern China, and the commonly used benzimidazole fungicides, such as carbendazim and thiophanate, have almost lost the value in preventing and controlling *fusarium* head blight. Furthermore, because the capability of fungicide-resistant pathogenic fungi in producing DON toxin is not less than five times the capability of sensitive strains, the harm of *fusarium* head blight and the risk of food safety in China are increasingly exacerbated. In order to reduce yield loss, farmers often double the use of fungicides, such as carbendazim, and as a result, fungicide resistance, pesticide residue, environment pollution and food safety problem are further exacerbated.

Therefore, the inventor finally accomplishes the present invention through a great deal of experimental research and analysis on the basis of summarizing the prior art.

SUMMARY OF THE INVENTION

Technical Problems to be Solved

The objective of the present invention is to provide a pesticide composition for preventing and controlling *fusarium* head blight.

The other objective of the present invention is to provide an agricultural fungicide for preventing and controlling *fusarium* head blight and decreasing grain DON toxin contamination.

Technical Solution

The present invention is implemented through the following technical solution.

The present invention relates to a pesticide composition for preventing and controlling *fusarium* head blight.

The pesticide composition comprises jinggangmycin and metconazole according to a weight ratio of (1-150):(1-20).

According to one preferred embodiment of the present invention, the pesticide composition comprises jinggangmycin and metconazole according to a weight ratio of (30-100):(3-18).

According to another preferred embodiment of the present invention, the pesticide composition comprises jinggangmycin and metconazole according to a weight ratio of (50-65):(6-16).

The present invention further relates to an agricultural fungicide for preventing and controlling *fusarium* head blight. The agricultural fungicide contains 0.1 to 90.0 percent by weight of pesticide composition, and the balance is a carrier and/or an adjuvant acceptable in pesticides.

According to one preferred embodiment of the present invention, the agricultural fungicide contains 10 to 75.0 percent by weight of pesticide composition, and the balance is the carrier and/or the adjuvant acceptable in pesticides.

According to another preferred embodiment of the present invention, the agricultural fungicide contains 26 to 58.0 percent by weight of pesticide composition, and the balance is the carrier and/or the adjuvant acceptable in pesticides.

According to another preferred embodiment of the present invention, the agricultural fungicide is a suspending agent, an emulsion in water, a microemulsion, a wettable powder or a water-dispersible granule.

According to another preferred embodiment of the present invention, the carrier is one or more of water, attapulgite, kaolin and light calcium carbonate.

According to another preferred embodiment of the present invention, the adjuvant is chosen from ethanol, methanol, ethylene glycol, propylene glycol, NNO-1, NNO-7, xanthan gum, polyethylene glycol, glycerol, nekal, sodium dodecyl sulfate, sodium dodecyl benzene sulfonate, ammonium sulfate, alkylphenol ethoxylates, alkylphenol polyoxyethylene ether phosphate, polyoxyethylene fatty acid, benzoic acid, sodium lignin sulfonate, carboxymethylcellulose and polyvinyl alcohol.

According to another preferred embodiment of the present invention, the *fusarium* head blight is wheat scab and barley scab, including bud rot, seedling blight, ear rot or ear blight of triticeae crops caused by *fusarium* pathogenic fungi (*Fusarium* spp.) of carbendazim-resistant fusaria.

The present invention is described in more detail below.

The present invention relates to a pesticide composition for preventing and controlling *fusarium* head blight.

The pesticide composition comprises jinggangmycin and metconazole according to a weight ratio of (1-150):(1-20).

The chemical structural formula of metconazole used in the present invention is as follows:

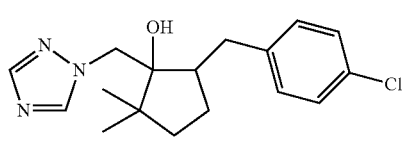 [SMILES: CC1(C)CCC(Cc2ccc(Cl)cc2)C1(O)Cn1cncn1]

Metconazole is a triazole ergosterol biosynthesis inhibitor, which comprises cis-isomers (1RS, 5SR) with high antifungal activity and trans-isomers with low activity, and metconazole used by the present invention is a mixture of cis-isomers and trans-isomers. Metconazole has high inhibitory activity for the growth of *fusarium* hyphae, and, mainly by inhibiting ergosterol biosynthesis, destroys the cell membrane permeability and membrane structure of fungi, strongly inhibiting the growth of the fungal hyphae. However, not only do metconazole acceptors Cyt.$P_{450}$ in different plant pathogenic fungue cells have structural diversity, but also a variety of regulatory and antagonistic physiological mechanisms exist, so that different fungi show different sensitivities. At present, this fungicide is mainly internationally used for preventing and controlling rust (*Puccinia* spp.), leaf blight or glume blight (*Septoria* spp.), net blotch (*Pyrenophora teres*) and scald (*Rhynchosporium secalis*) of grain crops, but only has a medium prevention and control effect on triticeae powdery mildew (*Erysiphe* spp.) and head blight (*Fusarium* spp.).

The chemical structural formula of jinggangmycin or validamycin used by the present invention is as follows:

Jinggangmycin is a secondary metabolite of actinomycetes, and contains six types of similar amino glucan glycoside derivatives A, B, C, D, E, F. A large number of domestic and foreign studies have shown that the component A is the main active component of jinggangmycin. Therefore, jinggangmycin in the present invention is jinggangmycin A.

Jinggangmycin shows interference specific to the development of hyphae at the tips of rhizoctonia fungi (Rhizoctonia spp.) among basidiomycetes in vitro. Therefore, since jinggangmycin was discovered in 1970s, jinggangmycin has always served as an agricultural antibiotic for specifically preventing and controlling plant diseases caused by rhizoctonia, or has been processed into mixtures along with pesticides for preventing and controlling other plant pests to control rhizoctonia (Rhizoctonia spp.) diseases. These rhizoctonia diseases mainly include rice sheath blight, wheat sheath blight and sheath blight or damping-off of other crops. In recent years, it has also been discovered that jinggangmycin can also be used for preventing and controlling false smut caused by hard-to-culture imperfect fungi (Ustilaginoidea virens).

As validamycin or jinggangmycin only shows specific antifungal activity on rhizoctonia in vitro and does not have antifungal activity on fusaria of head blight, people have always studied the selective mechanism of jinggangmycin with rhizoctonia as an object for decades, discovering that validamycin/jinggangmycin interferes with the inositol and trehalose metabolism of rhizoctonia, as a result, the structure of the cell wall is destroyed, rhizoctonia is prevented from infecting plants, and thereby jinggangmycin has a good protective effect. For decades, this antibiotic has always been limited to use for preventing and controlling rhizoctonia diseases of crops, especially rice sheath blight.

As everyone knows, fungicide-resistant pathogenic fungi can be easily screened out from specific fungicides with single effects, so the specific fungicides will lose application value shortly after being applied widely. The inventor has studied the risk of the fungicide resistance of rhizoctonia to selective jinggangmycin since 1980s, discovering that what is different from any other selective antibiotics and chemical fungicides with extremely high resistance risk is that jinggangmycin-resistant rhizoctonia cannot be screened out from jinggangmycin under both lab and field conditions. It can be inferred therefrom that besides interfering with known inositol and trehalose biosynthesis, jinggangmycin may also have other special disease-resistant effect mechanisms.

On the basis of studying the DON toxin biosynthesis pathway and regulatory mechanism of fusarium, the inventor carried out the screening of a large number of compounds for inhibiting DON toxin biosynthesis. In the screening process, it was surprisingly discovered that with certain treating dosage, jinggangmycin can strongly inhibit biochemical reaction in the early pathway of DON toxin biosynthesis of wheat scab fungi. Therefore, providing a technique for preventing and controlling fusarium head blight with a jinggangmycin and metconazole composition to reduce DON contamination has become an important objective of the present invention.

The inventor carries out the inhibition of the synthesis of the pathogenic factor DON of fusaria by jinggangmycin/validamycin and the screening of synergistic formulas of mixtures of jinggangmycin/validamycin and other various fungicides for preventing and controlling fusarium head blight in fields for the first time in the world, and creatively discovered that the jinggangmycin and metconazole composition has the advantages of outstanding synergism, DON toxin contamination reduction and great metconazole dosage reduction in preventing and controlling fusarium head blight.

In the pesticide composition of the present invention, if the amount of jinggangmycin is within a range from 1 part by weight to 150 parts by weight while the amount of metconazole is less than 1 part by weight, then the prevention and control effect on head blight will be decreased; if the amount of metconazole is greater than 20 parts by weight, then the synergistic effect will be decreased, and the pesticide composition has an inhibitory effect on the growth of wheat. Therefore, it is reasonable that the amount of metconazole is 1 to 20 parts by weight.

Likewise, if the amount of metconazole is within a range from 1 part by weight to 20 parts by weight while the amount of jinggangmycin is less than 1 part by weight, then the synergistic effect of jinggangmycin in preventing and controlling head blight and decreasing the toxin contamination level in cooperation with metconazole will be lost; if the amount of jinggangmycin is greater than 150 parts by weight, then cost will be increased, and the synergistic effect of jinggangmycin in preventing and controlling head blight and reducing toxin contamination in cooperation with metconazole will be decreased; and therefore, it is appropriate that the amount of jinggangmycin is 1 to 150 parts by weight.

Preferably, the pesticide composition comprises jinggangmycin and metconazole according to a weight ratio of (30-100):(3-18).

More preferably, the pesticide composition comprises jinggangmycin and metconazole according to a weight ratio of (50-65):(6-16).

Both jinggangmycin and metconazole which are used by the present invention are products which are sold in the market at present, such as 3%, 5% A, 20%, 40% A and 60% A jinggangmycin powders and aqueous solutions of Zhejiang Qianjiang Biochemical Co., Ltd. and metconazole produced by Jiangsu Gengyun Chemical Co., Ltd.

The present invention further relates to an agricultural fungicide preparation for preventing and controlling fusarium head blight. The agricultural fungicide contains 0.1 to 90.0 percent by weight of pesticide composition, and the balance is a carrier and/or an adjuvant acceptable in pesticides.

In the present invention, it should be understood that the pesticide carrier or adjuvant is an auxiliary substance which is used to improve the physical and chemical properties of the agent, enhance efficacy and facilitate transportation and storage when the pesticide preparation is processed or used, such as a wetting agent, an emulsifier, a dispersing agent, a binder, a stabilizer or a synergist. According to the present invention, any chemical substance which has these properties and does not have any adverse influence on the agricultural fungicide of the present invention can be used in the present invention, and they are all within the protection scope of the present invention.

The carrier used in the present invention, for example, is one or more of water, attapulgite, kaolin and light calcium carbonate. Besides, the present invention can also use other carriers which can meet the requirement of the present invention and are commonly used in the art.

For example, the adjuvant used by the present invention is chosen from ethanol, methanol, ethylene glycol, propylene glycol, NNO-1 (chemical name: naphthalene sulfonate formaldehyde condensate sodium salt), NNO-7 (chemical name: naphthalene sulfonate formaldehyde condensate calcium salt), xanthan gum, polyethylene glycol, glycerol, nekal, sodium dodecyl sulfate, sodium dodecyl benzene sulfonate, ammonium sulfate, alkylphenol ethoxylates, alkylphenol polyoxyethylene ether phosphate, polyoxyethylene fatty acid, benzoic acid, sodium lignin sulfonate, carboxymethylcellulose and polyvinyl alcohol. The adjuvant used by the present invention is a product which is sold widely in the market at present, such as dispersing agents sold with the product names "NNO-1" and "NNO-7" by Xinyi Feihuang Chemical Co., Ltd., butylnaphtalenesulfonic acid sodium salt emulsifying, dispersing and permeating agent sold with the product name "nekal" by Hubei Prosperity Galaxy Chemical Co., Ltd., alkylphenol ethoxylates solded by Shanghai Honesty Fine Chemical Co., Ltd., alkylphenol polyoxyethylene ether phosphate sold by Guangzhou XiLu Chemical Co., Ltd., polyoxyethylene fatty acid sold by Shandong Liangshan Hongtai Epoxidized Soybean Oil Co., Ltd. and carboxymethylcellulose sold by Jiangxi Pingxiang Mashan Additives Factory. Besides, the present invention can also use other adjuvants which can meet the requirement of the present invention and are commonly used in the art.

In the present invention, in the agricultural fungicide, if the amount of the pesticide composition is less than 0.1 percent, then the disease prevention effect will be decreased or the synergistic effect will be lost; if the amount of the pesticide composition is greater than 90.0 percent, then the synergistic effect will be lost or the disease prevention effect will be decreased; and therefore, it is reasonable that the amount of the pesticide composition is 0.1 to 90.0 percent.

Preferably, the agricultural fungicide contains 10 to 75 percent by weight of pesticide composition, and the balance is the carrier and/or the adjuvant acceptable in pesticides.

More preferably, the agricultural fungicide contains 26 to 58 percent by weight of pesticide composition, and the balance is the carrier and/or the adjuvant acceptable in pesticides.

In practical application, according to methods known by those skilled in the art, the fungicidal composition of the present invention and the carrier and/or the adjuvant can be prepared into agent forms adopted commonly in agriculture, such as a suspending agent, an emulsion in water, a microemulsion, a wettable powder or a water-dispersible granule.

While the suspending agent is prepared, the applicable carrier or adjuvant, for example, can be a dispersing agent chosen from alkyl naphthalene sulfonate, polycarboxylate and lignosulfonate, a wetting agent chosen from alkylphenol polyoxyethylene ether phosphate, phenethyl phenol polyoxyethylene ether phosphate, alkyl sulfate, alkyl sulfonate and naphthalene sulfonate, a thickening agent chosen from xanthan gum, aluminium-magnesium silicate and bentonite, a preservative chosen from benzoic acid and sodium benzoate, an organosilicon defoaming agnt and an antifreezing agent chosen from glycerol, urea, ethylene glycol and propylene glycol.

While the emulsion in water is prepared, the applicable carrier or adjuvant, for example, can be an emulsifier chosen from PESTICIDE EMULSIFIER 700 (alkyl phenol formaldehyde resin polyoxyethylene ether), PESTICIDE EMULSIFIER 2201 (calcium dibutylnaphthalenesulfonate), Span-60 (sorbitan monostearate) and EMULSIFIER T-60 (polyoxyethylene sorbitan monostearate), a solvent chosen from xylene, methylbenzene and cyclohexanone, a stabilizer chosen from triphenyl phosphite and epichlorohydrin, an antifreezing agent chosen from ethylene glycol, propylene glycol, glycerol and urea, a thickening agent chosen from aluminium-magnesium silicate, bentonite and xanthan gum or a preservative chosen from benzoic acid and sodium benzoate.

While the microemulsion is prepared, the applicable carrier or adjuvant, for example, can be an emulsifier chosen from calcium dodecyl benzene sulfonate (PESTICIDE EMULSIFIER 500), alkyl phenol formaldehyde resin polyoxyethylene ether (PESTICIDE EMULSIFIER 700), calcium dibutylnaphthalenesulfonate (PESTICIDE EMULSIFIER 220), sorbitan monostearate (Span-60), polysorbate 80 (Tween-80) and polyoxyethlene octylphenol (EMULSIFIER TX-10), a cosolvent chosen from methanol, isopropanol, n-butyl alcohol and ethyl alcohol, a solvent chosen from dimethylbenzene, methylbenzene, cyclohexanone and N-methylpyrrolidone or a stabilizer chosen from triphenyl phosphite and epichlorohydrin.

While the wettable powder is prepared, the applicable carrier or adjuvant, for example, can be a dispersing agent chosen from polycarboxylate, lignosulfonate and alkyl naphthalene sulfonate, a wetting agent chosen from alkyl sulfonate, alkyl sulfate and naphthalene sulfonate or a filler chosen from light calcium carbonate, talcum powder, diatomite, kaolin and attapulgite.

While the water-dispersible granule is prepared, the applicable carrier or adjuvant, for example, can be a dispersing agent chosen from polycarboxylate, lignosulfonate and alkyl naphthalene sulfonate, a wetting agent chosen from alkyl sulfate, polyoxyethylene alcohol, alkyl sulfonate and naphthalene sulfonate, a disintegrating agent chosen from citric acid, ammonium sulfate, glucose, urea and sodium bicarbonate, a binder chosen from corn starch, microcrystalline celluloses and diatomite or a filler chosen from light calcium carbonate, sepiolite, diatomite, kaolin, attapulgite and talcum powder.

His research results are respectively elaborated below.

I. Screening of Active Compounds for Inhibiting *Fusarium* Growth

The present invention adopts a conventional method of fungicide bioassay, jinggangmycin and metconazole are respectively prepared into 2 mg/mL of mother solution by using sterile water and methanol, a control agent, raw carbendazim, is dissolved into 0.1M/L of hydrochloric acid solution, phenamacril is dissolved in methanol, and thereby 2 mg/mL of mother solution is prepared. When potato dextrose agar media (PDA) are cooled to the temperature of about 45□, jinggangmycin and metconazole are respectively added in to designed concentrations (see Table 1), and are then poured into culture dishes to produce plates treated by the different agents, the process is repeated each time after three dishes are treated, hyphal clumps of wild sensitive strains (sensitive strains for short) and carbendazim-resistant and phenamacril-resistant strains (fungicide-resistant strains for short) of common *fusarium graminearum* and *fusarium asiaticum* causing *fusarium* head blight are inoculated, and are cultured under the temperature of 25□ for four days, the diameters of the fungal colonies are measured by a crossing method, effective medium dosages ($ED_{50}$ values) when different treatments inhibit the growth of the pathogenic fungi by 50 percent are calculated, and antifungal activities are compared.

The experimental result indicates that no matter whether jinggangmycin is used alone or mixed with metconazole, jinggangmycin almost does not have inhibitory activity on the growth of the sensitive strains and fungicide-resistant strains of the two types of fusaria causing head blight in vitro, and only when the concentration of jinggangmycin is as high as 50 μg/mL can jinggangmycin have 6.5 to 7.8 percent of inhibitory effect on the growth of the two types of fusaria. However, metconazole has a similar strong inhibitory effect on the hyphal growth of the sensitive strains and fungicide-resistant strains of the two types of fusaria, and the inhibitory effect of 0.125 μg/mL of metconazole for treatment on hyphal growth can exceed 50 percent. Jinggangmycin does not have a synergistic effect for metconazole in inhibiting hyphal growth in vitro (Table 1).

According to growth inhibition rates of the wild sensitive strains and carbendazim-resistant and phenamacril-resistant strains of *fusarium asiaticum* and *fusarium graminearum* treated by different doses of metconazole, an effective medium dosage ($ED_{50}$) of metconazole for inhibiting the growth of the different fungicide-sensitive strains is calculated, a result shows that the sensitivities of the sensitive strains, the carbendazim-resistant strains and the phenamacril-resistant strains to metconazole are similar, $ED_{50}$ is 0.11 to 0.12 μg/mL, and a experimental result is listed in Table 2.

With $ED_{50}$ of the agents as parameters, the activities of the different fungicides in inhibiting the growth of the fusaria are compared, and it is discovered that the activity of metconazole is about four times the activity ($ED_{50}$ is 0.45 μg/mL for both types of fusaria) of carbendazim on the sensitive strains and about 1.5 times the activity ($ED_{50}$ is 0.165 μg/mL for both types of fusaria) of phenamacril on the sensitive strains. The result indicates that metconazole has strong activity in inhibiting the growth of the wild sensitive strains and the carbendazim-resistant and phenamacril-resistant fusaria, helping to decrease the contamination level of DON toxin infecting grains and prevent and control fungicide-resistant diseases.

TABLE 1

Influence of Jinggangmycin and Metconazole on Growth of Sensitive Strains of Two types of Fusaria In Vitro

| Strains | | Average Fungal Colony Diameter (mm) | | Growth Inhibition Rate (%) | |
|---|---|---|---|---|---|
| Agents | Concentration (μg/mL) | F.g* | F.a* | F.g | F.a |
| Jinggangmycin A | 0.1 | 76.3 | 76.3 | / | / |
| | 1.0 | 76.2 | 76.3 | / | / |
| | 10.0 | 75.4 | 75.6 | / | / |
| | 50.0 | 70.3 | 69.4 | 6.5 | 7.8 |
| Metconazole | 0.0625 | 52.1 | 52.2 | 30.7 | 30.7 |
| | 0.125 | 31.2 | 31.2 | 58.5 | 58.6 |
| | 0.25 | 18.3 | 18.4 | 75.7 | 75.6 |
| | 0.5 | 8.2 | 8.1 | 89.1 | 89.2 |
| | 1.0 | 3.0 | 3.1 | 96.0 | 95.9 |
| Jinggangmycin A + Metconazole | 0.1 + 0.125 | 32.3 | 32.2 | 57.0 | 57.2 |
| | 1.0 + 0.125 | 32.2 | 32.3 | 57.2 | 57.1 |
| | 10.0 + 0.125 | 31.4 | 31.3 | 58.2 | 58.4 |
| | 50.0 + 0.125 | 30.1 | 30.1 | 60.0 | 60.0 |
| | 0.1 + 0.25 | 19.3 | 19.2 | 74.3 | 74.5 |
| | 1.0 + 0.25 | 18.7 | 18.6 | 75.1 | 75.3 |
| | 10.0 + 0.25 | 18.7 | 18.8 | 75.1 | 75.0 |
| | 50.0 + 0.25 | 16.0 | 15.6 | 78.7 | 79.3 |
| Comparison | 0 | 75.2 | 75.3 | / | / |

*F.g and F.a are abbreviations of *Fusarium graminearum* and *Fusarium asiaticum*, similarly hereinafter.

TABLE 2

Growth Inhibition Activity of Metconazole on Sensitive Strains and Carbendazim-resistant and Phenamacril-resistant Strains of Two Types of Fusaria

| | Strains | | | | | |
|---|---|---|---|---|---|---|
| | F.g sensitive strains | F.g carbendazim-resistant strains | F.g phenamacril-resistant strains | F.a sensitive strains | F.a carbendazim-resistant strains | F.a phenamacril-resistant strains |
| $ED_{50}$ (μg/mL) | 0.117 | 0.113 | 0.115 | 0.114 | 0.112 | 0.116 |

II. Inhibitory Activity of Jinggangmycin on Toxin Biosynthesis Capability of Fusaria As the fungicide sensitivities of *fusarium graminearum* and *fusarium asiaticum* to jinggangmycin and metconazole are the same, the inventor chooses *fusarium asiaticum* with higher toxin synthesis capability (the weight of synthesized DON per unit fungus amount, μgDON/g by dry weight of hyphae) as a material to further study toxin synthesis. Carbendazim-resistant *fusarium asiaticum* causing *fusarium* head blight is inoculated into 3 percent of sterile mung bean soup, the solution is shaken for culture under the temperature of 25□ and 12/24 hours of scattered light for ten days, and conidia are collected centrifugally. The conidia are inoculated into potato sucrose (PS) culture solutions containing different doses of jinggangmycin according to final $10^6$/mL and shaken to be cultured under the temperature of 25□ and 12/24 hours of scattered light, cultures are filtered after seven and fourteen days, toxin contents in the culture solutions are assayed respectively and the dry weights of hyphae are measured, and toxin synthesis capabilities (the amount of toxin produced per unit weight of hyphae) are analyzed.

Toxin Determination Method: The culture filtrate is equal-volume extracted with ethyl acetate for two times, the extracts are combined, and then depressurized, distilled and dried, the combined extract is dissolved by 1 mL of acetonitrile and transferred into a new centrifuge tube, and after being distilled and dried again, the solution is stored under −20□ for later assay. During assay, 100 μL of TMS derivatization reagent (TMSI:TMCS=100:1) is added, 1 mL of ultrapure water is added after 10 minutes of uniform mixing, supernate is extracted and added into a GC sample bottle after shaking for layering, and a gas chromatograph (GC-ECD) with an electron capture detector is used to carry out toxin content assay. With a DON reagent of Sigma as a standard sample, a standard curve is created, and DON contents, including DON, 3ADON and 15ADON, in the culture solutions are calculated. Meanwhile, the filtered hyphae are dried to constant weights under 80□, and the dry weights of the hyphae are measured. In addition, after seven days of shaking for culture, the hyphae are taken out, and the expression levels of the key gene Tri5 for toxin synthesis are assayed.

It is discovered from an experimental result (Table 3) that the hyphal growths of the head blight fungi increase as culture time extends, but, when shaken to be cultured in the media treated by the different doses of jinggangmycin, hyphal growths are not notably changed in comparison with that of the blank control. It is indicated that jinggangmycin does not have the inhibitory effect on the growth of the head blight fungi cultured in liquid, which is the same as a linear growth rate determination result on the PDA plates. However, it is discovered for the first time that the amount (1 μg DON/g by dry weight of hyphae) of DON toxin synthesized per unit hyphal weight is remarkably decreased as the treating dosage of jinggangmycin is increased. Moreover, the inhibitory effect of jinggangmycin on DON synthesis decreases as culture time extends, and especially, the decreasing amplitude of low-concentration treatment is greater. It is indicated that jinggangmycin may be degraded as experimental time extends, and as a result, the inhibitory effect on toxin biosynthesis may be decreased.

According to toxin synthesis gene expression level analysis after seven days of treatment, it is creatively discovered that although jinggangmycin does not have adverse influence on the growth and hyphal morphology of fusaria in vitro, a very low treating dose of jinggangmycin can strongly inhibit the expression of the key gene tri5 for DON toxin synthesis, weakening the toxin biosynthesis capability of thalli and reducing DON biosynthesis, and an experimental result is listed in Table 4.

TABLE 3

Effect of Jinggangmycin in Inhibiting DON Toxin Synthesis Capability of Fusaria

| Treating Dosage of Jinggangmycin (μg/ml) | Toxin Production Capability of Hyphae (μgDON/g by dry weight of hyphae) | | DON Biosynthesis Inhibition Rate (%) | |
|---|---|---|---|---|
| | 7 Days | 14 Days | 7 Days | 14 Days |
| 0 | 88.0 | 52.32 | / | / |
| 1 | 62.82 | 51.43 | 28.61 | 1.70 |
| 10 | 56.76 | 48.20 | 35.50 | 7.87 |
| 100 | 48.23 | 36.68 | 45.19 | 29.89 |
| 1000 | 30.35 | 22.52 | 65.51 | 56.96 |
| 10000 | 21.23 | 12.85 | 75.88 | 75.44 |

TABLE 4

Influence of Jinggangmycin on Gene Expression of DON Synthesis Gene Tri5 of Fusaria

| Treating Dosage of Jinggangmycin (μg/ml) | Relative Expression Level of Tri5 Gene | Rate of Inhibition on Relative Expression Level of Tri5 Gene (%) |
|---|---|---|
| 0 | 1 | / |
| 1 | 0.41 | 59 |
| 10 | 0.34 | 66 |
| 100 | 0.16 | 84 |
| 1000 | 0.13 | 87 |
| 10000 | 0.10 | 90 |

III. Synergistic Effect of Metconazole for Jinggangmycin in Inhibiting DON Toxin Biosynthesis Capability of Fusaria Metconazole treatment can destroy the cell membrane permeability of the head blight fungi, inhibiting the growth of hyphae. Metconazole and jinggangmycin composition treatment can enhance the absorption and utilization of jinggangmycin by the pathogenic fungi. While the research content II determines the inhibition of jinggangmycin on DON toxin biosynthesis of the fusaria, inhibitory effects of jinggangmycin on the DON toxin biosynthesis capability of *fusarium asiaticum* under the existence of 0.1 μg/mL of metconazole are determined after seven and fourteen days of culture, and the synergistic effect of metconazole for jinggangmycin in inhibiting DON toxin biosynthesis is analyzed. The DON assay method is the same as that of the research content II.

It has been known from the research contents I and II that 0.1 μg/ml of metconazole for treatment alone has an inhibition rate approximating 50 percent on the hyphal growth of the head blight fungi. It can be seen from the result in Table 5 that 0.1 μg/ml of metconazole does not have significant inhibitory effects on the toxin biosynthesis capability of the fusaria in comparison with the toxin biosynthesis capability of the blank control after seven and fourteen days of treatment, which indicates that metconazole only has hyphal growth inhibition activity, and has no inhibitory effect on toxin synthesis capability. Nevertheless, when 0.1 μg/ml of metconazole exists in each treatment concentration, the inhibitory effect of jinggangmycin on DON toxin biosynthesis capability is greatly enhanced. Moreover, as culture time extends, the decreasing speed of the inhibitory effect of jinggangmycin on toxin synthesis capability is remarkably lower than that of control treatment without metconazole, and in particular, the synergistic effect for low-concentration jinggangmycin treatment and the prolonging of action time are more obvious. Based on the results of the simultaneous experiments in Table 3, synergistic effects for jinggangmycin in inhibiting the toxin biosynthesis of the fusaria after seven and fourteen days of treatment under the existence of 0.10 μg/mL of metconazole are calculated, and results are listed in Table 5. These results indicate: (1) jinggangmycin has a strong effect in decreasing the DON toxin biosynthesis capability of the fusaria, while metconazole does not have this effect; (2) metconazole has an obvious synergistic effect for jinggangmycin in inhibiting the toxin biosynthesis of the fusaria, and as the treating dosage of jinggangmycin is reduced, the synergistic effect is enhanced; (3) metconazole can prolong the time of the inhibitory effect of jinggangmycin on the toxin synthesis of the fusaria, and the synergistic effect is enhanced as the time of treatment extends.

TABLE 5

Synergistic Effect of 0.1 μg/mL of Metconazole for Jinggangmycin in Inhibiting DON Toxin Synthesis of Wheat Srab Fungi

| Treating Dosage of Jinggangmycin + Metconazole | Toxin Production Capability (μgDON/g by dry weight of hyphae) | | DON Biosynthesis Inhibition Rate (%) | | Synergistic coefficient of 0.1 μg/ml of Metconazole for Jinggangmycin in Inhibiting DON Synthesis * | |
|---|---|---|---|---|---|---|
| (μg/ml) | 7 Days | 14 Days | 7 Days | 14 Days | 7 Days | 14 Days |
| 0 + 0 | 88.00 | 52.32 | / | / | / | / |
| 0 + 0.1 | 87.42 | 52.50 | 0.66 | −0.34 | / | / |
| 1 + 0.1 | 47.20 | 45.15 | 46.36 | 13.70 | 162.0 | 805.9 |
| 10 + 0.1 | 26.06 | 27.21 | 70.39 | 47.99 | 198.3 | 609.8 |
| 100 + 0.1 | 15.13 | 10.08 | 82.81 | 80.73 | 180.4 | 270.1 |
| 1000 + 0.1 | 8.65 | 5.82 | 90.17 | 88.88 | 137.6 | 156.0 |
| 10000 + 0.1 | 5.85 | 3.12 | 93.35 | 94.04 | 123.0 | 124.7 |

* Synergistic Coefficient Calculation Method: When 0.1 μg/ml of metconazole exists, an inhibition rate of jinggangmycin on toxin synthesis is divided by a toxin synthesis inhibition rate (Table 3) of a corresponding dose of jinggangmycin for treatment alone, and the result is multiplied by 100.

IV. Effect and Synergistic Effect of Jinggangmycin and Metconazole Composition Suspending Agent in Treating Seeds to Prevent and Control Head Blight and Other Diseases at Wheat Seedling Stage According to weight ratios of jinggangmycin to metconazole which are 1:1.5, 10:1.5, 100:1.5, 1:1, 10:1, 100:1, 2:1, 20:1, 200:1, 5:1, 50:1 and 500:1, composition suspending agent samples, the contents of which are 3% (1:1.5, 1:1, 2:1), 5% (10:1.5, 10:1, 5:1), 10% (50:1, 100:1, 20:1) and 20% (100:1.5, 200:1, 500:1), are prepared respectively. In a sample preparation method, raw metconazole and raw jinggangmycin are mixed according to the above-mentioned weight ratios, added into a solution containing 40 percent by weight of water, 8 percent by weight of ethylene glycol and propylene glycol mixed solvent (volume ratio: 1:1), 1.0 percent by weight of NNO-1 and 1.5 percent by weight of NNO-7 dispersing agents (produced by Xinyi Feihuang Chemical Co., Ltd.), 0.5 percent by weight of xanthan gum binder and 1 percent by weight of polyethylene glycol and, finally, supplemented with water to 100 percent, and the granule diameter of agents milled to 90 percent by a sand mill is less than or equal to 5 μm.

According to dosages of the single agents in a mixed agent for treatment per 100 kg of seeds, single dosages of jinggangmycin and metconazole in corresponding dosages are designed (see Table 6), and before seeding, the samples are respectively mixed with the seeds according to 5 L of liquor per 100 kg of seeds to treat the wheat seeds infected by wheat scab fungi after being diluted by water. Twenty five seeds are sowed per pot with the diameter of 20 cm, each treatment is repeated for ten pots, and the seeds are put into a greenhouse for culture. Ten days after emergence, the rate of emergence and the rate of dead seedlings are checked, and prevention and control effects on bud rot and seedling blight caused by the head blight fungi are calculated. Meanwhile, ten seedlings which are uniform in growth are kept, furthermore, a bran medium containing rhizoctonia cerealis is inoculated in substrate, powdery mildew fungus and leaf rust fungus spores are inoculated on leaves, one hundred wheat seedlings per treatment are investigated fourteen days after inoculation, and incidences of sheath blight, powdery mildew and rust and prevention and control effects are calculated. Meanwhile, according to prevention effects of the single agents on bud rot and seedling blight caused by the head blight fungi, theoretical prevention effect (E=X+ (100−X)Y/100, wherein E is the theoretical prevention effect, X is the prevention effect of the single jinggangmycin agent, and Y is the prevention effect of the single metconazole agent) and synergistic coefficient (actual prevention effect of the composition in application÷theoretical prevention effect×100) of the composition are calculated by the Abbott (1925) method, and results can be seen in Table 6.

TABLE 6

Effect and Synergistic Effect of Jinggangmycin and Metconazole Composition Suspending Agent in Treating Seeds to Prevent and Control Wheat Diseases

| Serial Number | Treating Dosage Per 100 kg of Seeds (g ai. agent) Jinggangmycin | Metconazole | Incidence Prevention Effect % Head Blight | Sheath Blight | Powdery Mildew | Rust | Prevention and Control of Head Blight Theoretical Prevention Effect % | Synergistic Coefficient * |
|---|---|---|---|---|---|---|---|---|
|  | 10 | 15 | 100 | 98.5 | 90.5 | 98.5 | 60.5 | 165.3 |
|  | 100 | 15 | 99.5 | 99.5 | 90.0 | 98.5 | 66.03 | 150.7 |
|  | 1000 | 15 | 100 | 100 | 91.5 | 99.5 | 68.60 | 145.8 |
|  | 10 | 10 | 95.0 | 97.0 | 82.5 | 94.5 | 58.5 | 162.4 |
|  | 100 | 10 | 96.5 | 99.0 | 82.0 | 95.5 | 64.31 | 150.1 |
|  | 1000 | 10 | 99.5 | 100 | 82.5 | 97.5 | 67.0 | 148.5 |
|  | 10 | 5 | 87.5 | 80.5 | 74.0 | 86.0 | 46.0 | 175.0 |
|  | 100 | 5 | 89.5 | 86.0 | 75.5 | 88.0 | 53.56 | 167.1 |
|  | 1000 | 5 | 94.5 | 95.5 | 74.5 | 89.5 | 57.07 | 165.6 |
| 0 | 10 | 2 | 32.0 | 60.5 | 60.5 | 70.0 | 15.0 | 213.3 |
| 1 | 100 | 2 | 51.5 | 75.0 | 62.0 | 83.5 | 26.9 | 191.4 |
| 2 | 1000 | 2 | 58.5 | 81.5 | 64.0 | 83.0 | 32.43 | 180.4 |
| 3 | 10 | 0 | 0 | 10.5 | 0 | 0 | / | / |
| 4 | 100 | 0 | 14.0 | 26.0 | 0 | 0 | / | / |
| 5 | 1000 | 0 | 20.5 | 56.0 | 6.5 | 4.5 | / | / |
| 6 | 0 | 15 | 60.5 | 35.0 | 75.0 | 85.5 | / | / |
| 7 | 0 | 10 | 58.5 | 19.5 | 68.5 | 82.0 | / | / |
| 8 | 0 | 5 | 46.0 | 14.5 | 61.0 | 71.0 | / | / |
| 9 | 0 | 2 | 15.0 | 11.0 | 40.0 | 54.5 | / | / |
| 0 | Blank Control Incidence % |  | 16.5 | 21.5 | 65.0 | 24.0 | / | / |

* Abbott believed that if the ratio of the actual prevention effect to theoretical prevention effect of a composition is greater than 1 (or a synergistic coefficient is greater than 100), then the composition has a synergistic effect (similarly hereinafter) (Abbott, 1925).

The above-mentioned experimental result indicates that when being mixed with the wheat seeds to treat the wheat seeds infected by head blight, the jinggangmycin and metconazole composition not only can effectively prevent and control bud rot and seedling blight caused by the head blight fungi, but also has an excellent synergistic effect in preventing and controlling seedling blight caused by the head blight fungi within the ranges of the experimental dosages for treatment (10-1000 g ai of jinggangmycin and 2-15 g ai of metconazole/100 kg of seeds), the synergistic coefficient is far greater than 100, and the synergistic effect is extremely outstanding. The single jinggangmycin agent has a certain prevention effect on sheath blight, but is almost ineffective to powdery mildew and rust; and except having a good prevention effect on rust at the seedling stage, the single metconazole agent only has a medium prevention effect on head blight, sheath blight and powdery mildew at the seedling stage, but can show an obvious synergistic effect in preventing and controlling the above-mentioned diseases when mixed with jinggangmycin.

V. Synergistic Effect and Toxin-Reducing Effect of Jinggangmycin and Metconazole Composition Suspending Agent in Preventing and Controlling Wheat Scab According to weight ratios of jinggangmycin to metconazole which are 1:50, 1:20, 1:3, 1:2, 1:1.5, 1:1, 2:1, 5:1, 5:1.5, 50:3, 10:1, 10:1.5, 50:2.5, 50:1.5 and 50:1, experimental composition suspending agent samples, the contents of which are 20% (1:50, 1:20, 1:3, 1:2, 1:1.5, 1:1, 2:1, 5:1, 5:1.5) and 40% (10:1, 10:1.5, 50:3, 50:2.5, 50:1.5, 50:1) by weight, are prepared respectively. In a sample preparation method, after raw metconazole and raw jinggangmycin are mixed according to the above-mentioned weight ratios, each mixture is added into a solution containing 5 percent by weight of ethylene glycol and propylene glycol mixed solvent (volume ratio: 1:1), 2 percent by weight of glycerol, 1.0 percent by weight of NNO-1, 1.5 percent by weight of NNO-7 dispersing agent, 3 percent by weight of sodium dodecyl sulfate and a small amount of water, finally, the solution is supplemented with water to 100 percent, and the granule diameter of agents milled to 90 percent by a sand mill is less than or equal to 5 μm.

Different dosages of the jinggangmycin and metconazole composition used per mu are designed, and meanwhile, corresponding single-agent treatments are designed according to dosages of the single agents in each mixed agent in use. In April, 2013, experimental screening for preventing and controlling head blight in fields was carried out in Jiangsu White Horse Lake Farm, the wheat variety was Huaimai 22, each agent sample was mixed with water and sprayed for treatment at the initial stage of wheat blooming, five days later the agent sample is sprayed for the second time, and the amount of sprayed water per mu was 50 kg. Each treatment was repeated for three plots, and the area of each plot was 50 square meters. Meanwhile, 80 g of carbendazim wettable powder which was 50 percent was used as a control agent for treatment per mu. According to a corresponding method specified by the industrial standard of Guidelines for the Field Efficacy Trials of Fungicides issued by the Ministry of Agriculture, the occurrence of wheat scab was investigated at the stage of milky ripeness, and according to the actual effect of each treatment in preventing and controlling head blight, the synergistic effects of the composition were calculated. According to the Abbott (ditto, 1925) method, theoretical prevention effect (E=X+(100−X) Y/100, wherein E is the theoretical prevention effect, X is the prevention effect of the single jinggangmycin agent, and Y is the prevention effect of the single metconazole agent) and synergistic coefficient (actual prevention effect of the composition in application÷theoretical prevention effect× 100) of the composition were calculated.

Toxin Determination Method: Two hundred wheat ears were sampled every five treated points at the stage of wax ripeness, and were threshed indoors, and after drying, 30 g of kernels were sampled randomly and ground. According to Goswami and Kistler methods, 5 g of flour was put into a centrifuge tube, 20 mL of extract of acetonitrile and water (84:16) was added into the flour and uniformly mixed by a vortex mixer, the solution was then shaken on a shaker for 24 hours, and was centrifuged at 5000 rpm for 10 minutes, and 2 mL of supernate was blow-dried by nitrogen in an Eppendorf centrifuge tube and preserved under −20□. During assay, 100 μL of TMS derivatization reagent (TMSI:TMCS=100:1) was added, 1 mL of ultrapure water was added after 10 minutes of uniform mixing, supernate was extracted and added into a GC sample bottle after shaking for layering, and a gas chromatograph (GC-ECD) with an electron capture detector was used to carry out toxin content assay.

Kernel-inflicting Fungus Amount Determination Method: 2 g of flour for toxin assay was put into a 50 mL centrifuge tube, added with 20 percent of CTAB pathogenic fungus DNA extraction buffer, then added with 50 μL of protease K and 30 μL of RNA enzyme and mixed sufficiently, the solution was centrifuged at 10000 rpm for 10 minutes after being incubated under 65□ for 3 hours, 20 mL of supernate was completely transferred into a 50 mL centrifuge tube, then added with phenol, chloroform and isoamyl alcohol (25:24:1) of the same volume, shaken violently and centrifuged at 10000 rpm for 5 minutes, 10 mL of supernate was added with 3 molL$^{-1}$ of cold sodium acetate accounting for one tenth of the volume and absolute ethyl alcohol two times the volume, precipitation was carried out under −20□ for 24 hours, centrifugation was carried out at 10000 rpm for 10 minutes, precipitate was eluted two times by 20 mL of 70 percent ethyl alcohol, the precipitate was dissolved into 500 μL of TE solution after being dried, and the DNA template was stored under −20□. Primers were designed according to the key gene Tri5 for DON synthesis, DNA in a sample is amplified by adopting real time quantitative PCR, moreover, the Tri5 DNA content (μgDNA/g of wheat) in each gram of wheat sample was calculated, and the inhibitory effect of each treatment of the composition on the toxin synthesis capability of thalli was calculated. The result can be seen in Table 7.

TABLE 7

Synergistic Effect of Jinggangmycin and Metconazole Composition Suspending Agent in Preventing and Controlling Wheat Scab and Effect of Jinggangmycin and Metconazol Composition Suspending Agent in Reducing DON Toxin Contamination

| Serial Number | Treating Dosage (g ai. agent/mu) Jinggangmycin | Metconazole | Disease Index Prevention Effect % Actual Prevention Effect | Theoretical Prevention Effect | Synergistic Coefficient | DON Synthesis Capability (μg of toxin/g of DNA) | Grain Toxin Content (μg of toxin/g of kernels) | DON Contamination Reduction Rate % |
|---|---|---|---|---|---|---|---|---|
| 1 | 0.5 | 25 | 98.0 | 85.2 | 115.0 | 21.40 | 0.26 | 97.5 |
| 2 | 1 | 20 | 93.3 | 75.7 | 123.2 | 20.11 | 0.34 | 96.8 |
| 3 | 5 | 5 | 80.3 | 48.42 | 154.4 | 15.29 | 0.82 | 92.3 |
| 4 | 5 | 10 | 90.1 | 58.34 | 157.9 | 14.89 | 0.28 | 97.4 |
| 5 | 5 | 15 | 96.2 | 73.71 | 130.5 | 14.85 | 0.21 | 98.0 |
| 6 | 10 | 3 | 66.0 | 41.30 | 159.8 | 8.80 | 1.51 | 85.8 |
| 7 | 10 | 5 | 80.6 | 50.55 | 159.4 | 8.28 | 0.43 | 95.9 |
| 8 | 10 | 10 | 94.2 | 60.06 | 156.8 | 7.93 | 0.32 | 97.0 |
| 9 | 10 | 15 | 98.1 | 74.80 | 131.1 | 8.26 | 0.27 | 97.5 |
| 10 | 50 | 3 | 75.2 | 49.65 | 151.5 | 6.01 | 1.10 | 89.6 |
| 11 | 50 | 5 | 88.5 | 57.59 | 153.7 | 5.92 | 0.37 | 96.5 |
| 12 | 50 | 10 | 94.3 | 65.75 | 143.4 | 5.73 | 0.20 | 98.1 |
| 13 | 50 | 15 | 98.2 | 78.39 | 125.3 | 5.84 | 0.18 | 98.3 |
| 14 | 100 | 3 | 80.8 | 53.69 | 150.5 | 3.76 | 0.65 | 93.9 |
| 15 | 100 | 5 | 93.7 | 60.99 | 1.536 | 3.35 | 0.21 | 98.0 |
| 16 | 100 | 10 | 94.3 | 68.5 | 137.7 | 3.55 | 0.23 | 97.8 |
| 17 | 100 | 15 | 97.2 | 80.13 | 121.3 | 3.28 | 0.20 | 98.1 |
| 18 | 150 | 3 | 87.9 | 59.31 | 148.2 | 3.03 | 0.31 | 97.1 |
| 19 | 0.5 | / | 0 | / | / | 21.52 | 9.4 | 11.3 |
| 20 | 1 | / | 0 | / | / | 20.15 | 8.9 | 16.0 |
| 21 | 5 | / | 10.6 | / | / | 15.05 | 8.6 | 18.9 |
| 22 | 10 | / | 14.3 | / | / | 8.46 | 6.6 | 37.7 |
| 23 | 50 | / | 26.5 | / | / | 5.89 | 4.7 | 55.7 |
| 24 | 100 | / | 32.4 | / | / | 3.42 | 4.5 | 57.5 |
| 25 | 150 | / | 40.6 | / | / | 2.88 | 4.0 | 62.3 |
| 26 | / | 3 | 31.5 | / | / | 20.16 | 5.8 | 45.3 |
| 27 | / | 5 | 42.3 | / | / | 19.80 | 4.9 | 53.8 |
| 28 | / | 10 | 53.4 | / | / | 19.96 | 4.2 | 60.4 |
| 29 | / | 15 | 70.6 | / | / | 19.54 | 3.6 | 66.0 |
| 30 | / | 20 | 75.7 | / | / | 19.20 | 1.9 | 82.1 |
| 31 | / | 25 | 85.2 | / | / | 19.38 | 0.42 | 96.0 |
| 32 | Control Agent: Carbendazim 40 g a.i. | | 67.5 | | | 28.94 | 4.4 | 58.5 |
| 33 | Blank Control Disease Index | | 47.2 | / | / | 21.51 | 10.6 | / |

The field screening and experiment results of the synergistic effect of the composition for preventing and controlling *fusarium* head blight in the present invention indicate that when the jinggangmycin and metconazole composition is sprayed from the initial stage of wheat blooming to the filling stage and the mixed agent of 1 g to 150 g of active jinggangmycin ingredient and 2 g to 20 g of active metconazole ingredient is used per mu, not only does the jinggangmycin and metconazole composition have an outstanding synergistic effect (the synergistic coefficient is greater than 100) in preventing and controlling head blight, but also, after being applied, the jinggangmycin and metconazole composition has a remarkable synergistic effect in decreasing the DON contamination level of grains, the DON content can be reduced by 85 percent or above, and the DON contamination level can be controlled at a safe level not higher than 1 mg of DON/kg of grain. Meanwhile, the result of quantitative pathogenic fungus analysis for the inflected kernels also indicates that jinggangmycin has the effect of inhibiting the toxin synthesis capability of thalli while metconazole does not have such an effect. Although carbendazim has 67.5 percent of prevention effect on head blight when used for treatment alone, the toxin contamination level of grains is still 4.4 mg/kg of grains, and is only decreased by 58.5 percent in comparison with the blank control.

VI. Synergistic Effect and Toxin-Reducing Effect of Jinggangmycin and Metconazole Composition Suspending Agent in Preventing and Controlling Wheat Scab Adopting the experimental sample preparation methods of the invention research experiments IV and V, the present invention further designs treating dosages of the composition in use, and also designs single-agent treatments according to the dosages of jinggangmycin and metconazole in the composition. A field experiment was carried out in Jiangsu Xinyang Farm in 2013. Each agent was mixed with water and sprayed to treat Huaimai 22 at the initial stage of wheat blooming, the agent was sprayed for the second time 5 days later, and the amount of sprayed water per mu was 50 kg. Each treatment was repeated three times, and the area of each plot was 50 square meters. Meanwhile, 80 mL of carbendazim suspending agent which was 50 percent was used as a control agent for treatment per mu. According to a corresponding method specified by the relevant industrial standard of Guidelines for the Field Efficacy Trials of Fungicides issued by the Ministry of Agriculture, the occurrences of wheat scab, powdery mildew, rust and leaf blight were investigated at the stage of milky ripeness, disease indexes, prevention and control effects and synergistic effects for the prevention and control of head blight calculated by the above-mentioned Abbott (ditto, 1925) method were calculated, and the toxin assay method was the same as the method of the above-mentioned research V (results can be seen in Table 8).

TABLE 8

Effect of Jinggangmycin and Metconazole Composition Suspending Agent in Preventing and Controlling Wheat Diseases and Reducing Toxin Contamination of Grains

| Serial Number | Treating Dosage (g ai. agent/mu) Jinggangmycin | Metconazole | Disease Index Prevention Effect % Head Blight | Leaf Blight | Powdery Mildew | Rust | Theoretical Prevention Effect of Mixed Agent on Head Blight | Synergistic Coefficient of Mixed agent in Preventing and Controlling Head blight | Grain Toxin Content (μg of toxin/g of kernels) | DON Reduction Percentage (%) | Thousand Kernel Weight (g) |
|---|---|---|---|---|---|---|---|---|---|---|---|
| 1 | 1 | 15 | 92.2 | 90.5 | 85.3 | 97.8 | 65.8 | 140 | 0.20 | 98.4 | 44.2 |
| 2 | 3 | 10 | 91.9 | 87.2 | 80.1 | 90.4 | 61.3 | 150 | 0.26 | 97.9 | 44.6 |
| 3 | 5 | 5 | 77.4 | 78.6 | 75.6 | 84.3 | 51.3 | 151 | 0.87 | 93.1 | 44.3 |
| 4 | 5 | 10 | 80.7 | 85.2 | 79.6 | 87.4 | 63.5 | 127 | 0.32 | 97.5 | 44.4 |
| 5 | 5 | 15 | 92.5 | 87.9 | 83.8 | 95.3 | 67.7 | 137 | 0.28 | 97.8 | 44.3 |
| 6 | 10 | 3 | 73.2 | 74.5 | 74.2 | 75.5 | 47.6 | 154 | 1.14 | 91.0 | 43.8 |
| 7 | 10 | 10 | 85.9 | 86.9 | 80.5 | 84.8 | 66.4 | 129 | 0.41 | 96.7 | 44.7 |
| 8 | 10 | 15 | 91.3 | 94.8 | 84.9 | 90.2 | 70.3 | 130 | 0.29 | 97.7 | 45.6 |
| 9 | 50 | 3 | 81.5 | 82.8 | 68.5 | 83.4 | 55.4 | 147 | 0.68 | 94.6 | 44.8 |
| 10 | 50 | 10 | 90.6 | 86.4 | 79.4 | 88.6 | 71.4 | 127 | 0.26 | 97.9 | 44.7 |
| 11 | 50 | 15 | 94.6 | 96.1 | 83.6 | 98.2 | 83.1 | 114 | 0.22 | 98.3 | 45.2 |
| 12 | 100 | 5 | 82.6 | 84.4 | 80.8 | 85.6 | 65.0 | 127 | 0.35 | 97.2 | 45.2 |
| 13 | 100 | 10 | 91.8 | 90.2 | 80.1 | 87.8 | 73.8 | 124 | 0.28 | 97.8 | 45.7 |
| 14 | 100 | / | 32.2 | 8.3 | 7.5 | 4.9 | 32.2 | / | 3.36 | 73.3 | 43.2 |
| 15 | 50 | / | 26.1 | 7.8 | 4.5 | 3.8 | 26.1 | / | 3.80 | 69.8 | 42.8 |
| 16 | 10 | / | 13.3 | 7.8 | 0 | 0 | 13.3 | / | 4.98 | 60.5 | 42.9 |
| 17 | 5 | / | 5.6 | 0 | 0 | 0 | 5.6 | / | 7.92 | 37.1 | 42.6 |
| 18 | 3 | / | 0 | 0 | 0 | 0 | 0 | / | 8.98 | 28.7 | 42.0 |
| 19 | 1 | / | 0 | 0 | 0 | 0 | 0 | / | 11.05 | 12.3 | 39.6 |
| 20 | / | 15 | 65.8 | 76.6 | 78.7 | 83.8 | 65.8 | / | 1.46 | 88.4 | 43.4 |
| 21 | / | 10 | 61.3 | 71.1 | 74.3 | 78.4 | 61.3 | / | 2.53 | 79.9 | 42.8 |
| 22 | / | 5 | 48.4 | 52.1 | 70.2 | 66.7 | 48.4 | / | 3.60 | 71.4 | 42.4 |
| 23 | / | 3 | 39.6 | 38.2 | 48.6 | 41.9 | 39.6 | / | 4.21 | 66.6 | 40.4 |

TABLE 8-continued

Effect of Jinggangmycin and Metconazole Composition Suspending Agent in
Preventing and Controlling Wheat Diseases and Reducing Toxin Contamination of Grains

| Serial Number | Treating Dosage (g ai. agent/mu) | | Disease Index Prevention Effect % | | | | Theoretical Prevention Effect of Mixed Agent on Head Blight | Synergistic Coefficient of Mixed agent in Preventing and Controlling Head blight | Grain Toxin Content (μg of toxin/g of kernels) | DON Reduction Percentage (%) | Thousand Kernel Weight (g) |
|---|---|---|---|---|---|---|---|---|---|---|---|
| | Jinggangmycin | Metconazole | Head Blight | Leaf Blight | Powdery Mildew | Rust | | | | | |
| 24 | Carbendazim 40 g a.i. | | 38.6 | 48.5 | 52.6 | 61.2 | / | / | 5.67 | 55.0 | 41.6 |
| 25 | Control Disease Index | | 28.1 | 5.2 | 18.5 | 16.9 | / | / | 12.6 | / | 38.9 |

The field application results of the above-mentioned mixed agents indicate that when 1 g to 100 g of jinggangmycin as an active ingredient and 3 g to 15 g of metconazole as an active ingredient are used per mu to prevent and control wheat scab, the jinggangmycin and metconazole composition suspending agent not only has an excellent prevention and control effect on wheat scab, leaf blight, powdery mildew and rust, which is far better than that of commonly used carbendazim (the assay showed that pathogenic fungi which showed resistance to carbendazim in pathogenic fungus colonies in the experimental field accounted for 37.7 percent), moreover, the jinggangmycin and metconazole composition suspending agent has extremely remarkable synergistic and prevention and control effects on head blight caused by fungicide-resistant head blight fungi, and the result was similar to the field experiment result of White Horse Lake Farm in the same year. The difference between the effect of 3 g to 50 g of jinggangmycin and 3 g to 15 g of metconazole used per mu and the prevention effect of higher dosages is not great, DON toxin contamination can be controlled within a safe range, moreover, the dosage is less, the cost is low, the environment can be protected, and benefits are better. It is particularly worth noting that the thousand kernel weights of grains treated by all fungicides are obviously higher than that of the control, especially the jinggangmycin and metconazole composition for treatment increases thousand kernel weight by not less than 13.9 percent, and the yield-increasing effect is more prominent.

VII. Synergistic Effect of Jinggangmycin and Metconazole Composition Wettable Powder in Preventing and Controlling Wheat Scab and Toxin Contamination-Reducing Effect of Jinggangmycin and Metconazole Composition Wettable Powder According to the good result of the jinggangmycin and metconazole composition suspending agent in the field prevention and control of head blight and the treatment of other diseases, the present invention designs weight proportions which can help to reduce the dosage of the pesticide and cost, and prepares composition wettable powders with different contents of jinggangmycin and metconazole. Preparation method: After mixing according to a weight ratio of raw metconazole to raw jinggangmycin, the mixture is added with 30 percent by weight of attapulgite carrier, 1.0 percent by weight of NNO-1 dispersing agent, 3 percent by weight of nekal wetting agent and 2 percent by weight of sodium dodecyl benzene sulfonate surfactant and, finally, added with light calcium carbonate as a filler to 100 percent, and the mixture is milled by a sand mill and screened by a 300-mesh screen. Jinggangmycin and metconazole composition wettable powder samples, the contents of which are 20% (1:3, 1:2, 1:1.5, 1:1) and 60% (5:1, 10:3, 10:1), are prepared respectively.

Meanwhile, according to the dosages of the single agents in the composition used per mu, the single-agent treatments of jinggangmycin and metconazole and a common polyketone wettable powder control agent are designed. In 2014, each composition wettable powder sample was mixed with water and sprayed for treatment at the initial stage of wheat blooming, the composition wettable powder sample was sprayed for the second time 5 days later, and the amount of sprayed water per mu was 50 kg. Each treatment was repeated three times, and the area of each plot was 50 square meters. According to a corresponding method specified by Guidelines for the Field Efficacy Trials of Fungicides, the occurrences of barley scab, powdery mildew, rust and leaf blight were investigated at the stage of milky ripeness, and disease indexes and prevention and control effects were calculated. Meanwhile, according to the Abbott (1925) method of the research content V, the synergistic effects of the mixed agents in preventing and controlling barley scab were calculated. One hundred and fifty wheat ears were sampled randomly every five treated points at the stage of wax ripeness, taken and threshed indoors and assayed according to the method of the research content V, and toxin contents of the kernels were calculated. The treating dosages, prevention effects, synergistic effects and influences of the agents on toxin content can be seen in Table 9.

TABLE 9

Effect of Jinggangmycin and Metconazole Composition Wettable Powder in Preventing and Controlling Barley Scab

| Serial Number | Treating Dosage (g ai. agent/mu) Jinggangmycin | Metconazole | Disease Index Prevention Effect % Head Blight | Leaf Blight | Powdery Mildew | Rust | Prevention and Control of Head Blight Theoretical Prevention Effect | Synergistic Coefficient | Grain Toxin Content (mg of DON/Kg of grain) | Toxin Reduction Percentage (%) |
|---|---|---|---|---|---|---|---|---|---|---|
| | 3 | 10 | 80.4 | 81.2 | 80.5 | 85.1 | 61.6 | 132 | 1.0 | 88.3 |
| | 5 | 15 | 84.0 | 87.3 | 84.6 | 96.4 | 67.4 | 125 | 0.83 | 90.3 |
| | 5 | 10 | 83.1 | 86.2 | 80.8 | 88.0 | 63.3 | 131 | 0.85 | 90.0 |
| | 10 | 15 | 90.3 | 93.6 | 86.2 | 91.0 | 70.2 | 129 | 0.66 | 92.3 |
| | 5 | 5 | 78.0 | 80.4 | 78.0 | 81.3 | 49.2 | 159 | 0.91 | 89.3 |
| | 10 | 10 | 85.8 | 86.7 | 81.6 | 85.4 | 66.4 | 129 | 0.78 | 90.9 |
| | 50 | 10 | 88.6 | 85.4 | 82.4 | 86.5 | 71.7 | 124 | 0.49 | 94.3 |
| | 10 | 3 | 75.2 | 72.4 | 70.2 | 73.1 | 41.0 | 183 | 0.80 | 90.6 |
| | 100 | 10 | 88.6 | 93.2 | 82.1 | 90.8 | 74.1 | 120 | 0.46 | 94.6 |
| 0 | 3 | / | 0 | 0 | 0 | 0 | / | / | 6.67 | 21.8 |
| 1 | 5 | / | 4.5 | 0 | 0 | 0 | / | / | 5.28 | 38.1 |
| 2 | 10 | / | 12.6 | 0 | 0 | 0 | / | / | 4.62 | 45.8 |
| 3 | 50 | / | 26.4 | 0 | 0 | 0 | / | / | 3.86 | 54.7 |
| 4 | 100 | / | 32.5 | 6.9 | 3.4 | 0 | / | / | 3.49 | 59.1 |
| 5 | / | 3 | 32.5 | 56.2 | 52.6 | 63.0 | / | / | 3.86 | 54.7 |
| 6 | / | 5 | 46.8 | 70.4 | 65.3 | 68.2 | / | / | 3.70 | 56.6 |
| 7 | / | 10 | 61.6 | 73.7 | 71.8 | 76.1 | / | / | 3.09 | 63.8 |
| 8 | / | 15 | 65.9 | 80.0 | 82.2 | 88.2 | / | / | 3.26 | 61.8 |
| 9 | Polyketone 30 g a.i. | | 67.3 | 62.6 | 74.1 | 73.3 | / | / | 5.86 | 31.3 |
| | Control Disease Index | | 20.5 | 25.3 | 14.4 | 8.6 | / | / | 8.53 | / |

The field application of the composition indicates that the single-agent treatment of the single metconazole agent has a good prevention effect on barley scab, leaf blight, powdery mildew and rust while, except having a low prevention effect on head blight, the single jinggangmycin agent almost has no effect on other diseases. Nevertheless, when the composition containing 3 g to 50 g ai of jinggangmycin and 3 g to 15 g ai of metconazole is used, the prevention effect on head blight, leaf blight, powdery mildew and rust is greatly enhanced, the prevention and control effect reaches not less than 80 to 90 percent, better than the effect of the common control agent polyketone, and the synergistic effect is outstanding. In particular, when 3 g to 50 g of active jinggangmycin ingredient and 3 g to 15 g of active metconazole ingredient are used per mu, the dosage of the metconazole chemical fungicide can be greatly reduced, the environmental pressure caused by pesticides can be decreased, and the toxin contamination of kernels can be reduced.

VIII. Effect of Jinggangmycin and Metconazole Wettable Powder Tank Mixture in Preventing and Controlling Wheat Diseases and Reducing Toxin Contamination 64 percent of jinggangmycin A soluble powder of Zhejiang Tonglu Huifeng Biochemical Co., Ltd and 20 percent of metconazole wettable powder processed by Nanjing Nannong Pesticide Technology Development Co., Ltd. on commission which are purchased from the market are adopted. Dosages of the needed active jinggangmycin ingredient and active metconazole ingredient for use are designed according to an experiment, the two types of agents are weighed respectively, one type of agent is first mixed with half of water for dilution, then mixed with the other type of agent, stirred and then added with the other half of the water, and after uniform mixing, the mixed agent is sprayed. The mixed agent is sprayed for the first time at the initial stage of wheat blooming, and is sprayed for the second time 5 days later, and the amount of sprayed water per mu is 50 kg. An experiment was carried out in Jiangsu Xinyang Farm in April, 2014, the wheat variety was Huaimai 33, each treatment was repeated three times, and the area of each plot was 50 square meters. A polyketone suspending agent was adopted as a control agent for treatment. According to a corresponding method specified by Guidelines for the Field Efficacy Trials of Fungicides, the occurrences of wheat scab, powdery mildew, rust and leaf blight were investigated at the stage of milky ripeness, and disease indexes and prevention and control effects were calculated. Synergistic effects and toxin assay are the same as the above-mentioned research, and treating dosages and prevention effects can be seen in Table 10.

TABLE 10

Effect of Jinggangmycin and Metconazole Wettable Powder Tank Mixture in Preventing and Controlling Wheat Diseases

| Serial Number | Treating Dosage (g ai. agent/mu) Jinggangmycin | Treating Dosage (g ai. agent/mu) Metconazole | Disease Index Prevention Effect % Head Blight | Disease Index Prevention Effect % Leaf Blight | Disease Index Prevention Effect % Powdery Mildew | Disease Index Prevention Effect % Rust | Theoretical Prevention Effect on Head Blight % | Synergistic Coefficient | Grain Toxin Content (μg/g of kernels) |
|---|---|---|---|---|---|---|---|---|---|
| 1 | 3 | 15 | 90.6 | 93.6 | 90.1 | 100 | 66.7 | 136 | 0.24 |
| 2 | 5 | 10 | 89.2 | 87.4 | 80.3 | 97.6 | 64.3 | 139 | 0.23 |
| 3 | 5 | 5 | 84.2 | 78.3 | 74.2 | 87.7 | 54.1 | 156 | 0.45 |
| 4 | 10 | 5 | 88.8 | 83.6 | 76.6 | 89.1 | 57.2 | 155 | 0.38 |
| 5 | 50 | 3 | 85.2 | 75.4 | 72.8 | 74.3 | 51.3 | 166 | 0.40 |
| 6 | 100 | 3 | 90.2 | 85.7 | 71.8 | 87.5 | 54.4 | 166 | 0.31 |
| 7 | 100 | / | 31.4 | 8.5 | 7.3 | 5.1 | 31.4 | / | 2.89 |
| 8 | 50 | / | 26.7 | 7.9 | 4.4 | 3.6 | 26.7 | / | 3.24 |
| 9 | 10 | / | 12.8 | 0 | 4.5 | 0 | 12.8 | / | 3.86 |
| 10 | 5 | / | 6.5 | 0 | 0 | 0 | 6.5 | / | 4.20 |
| 11 | 3 | / | 0 | 0 | 0 | 0 | 0 | / | 4.77 |
| 12 | / | 15 | 66.7 | 76.8 | 73.7 | 82.6 | 66.7 | / | 2.01 |
| 13 | / | 10 | 61.8 | 71.7 | 70.5 | 77.4 | 61.8 | / | 2.24 |
| 14 | / | 5 | 50.9 | 53.4 | 63.5 | 69.2 | 40.9 | / | 2.38 |
| 15 | / | 3 | 33.6 | 32.4 | 33.6 | 40.4 | 33.6 | / | 2.94 |
| 16 | Polyketone 57 g a.i. | | 69.4 | 72.1 | 75.3 | 74.6 | / | / | 3.16 |
| 17 | Blank Control Disease Index | | 45.6 | 18.4 | 20.6 | 24.8 | / | / | 5.84 |

The above-mentioned research results indicate that when the single jinggangmycin agent and the single metconazole agent in are mixed in a tank on spot and then sprayed, the effect of the treatment using 3 g to 100 g of active jinggangmycin ingredient per mu and the effect of the treatment using 3 g to 15 g of active metconazole ingredient per mu in preventing and controlling head blight are equivalent to the effect of a prepared mixed agent applied on barley and wheat, moreover, the synergistic effect on wheat scab, powdery mildew, rust and leaf blight is also obvious, and the prevention and control effect is better than that of polyketone. In particular, the synergistic effect on wheat scab is prominent, the results are similar to the results of the other examples, which is reflected in that within the experimental dosage rang, as the dosage of metconazole is reduced, the synergistic effect is enhanced. 3 g to 50 g of active jinggangmycin ingredient used per mu and 3 g to 15 g of active metconazole ingredient used per mu can both achieve an ideal effect in preventing and controlling head blight, controlling leaf blight, powdery mildew and rust and reducing DON toxin contamination.

In a word, *fusarium* head blight described in the present invention is wheat scab and barley scab, including bud rot, seedling blight, ear rot or ear blight of triticeae crops caused by *fusarium* pathogenic fungi (*Fusarium* spp.) of carbendazim-resistant fusaria.

The above-mentioned research results indicate that the composition containing 1 g to 150 g of active jinggangmycin ingredient and 1 g to 20 g of active metconazole ingredient used per mu has a remarkable synergistic effect in treating (coating or mixing) wheat seeds to prevent and control *fusarium* head blight before sowing, and moreover, the composition can also control powdery mildew, rust and sheath blight of triticeae; and when mixed with water and sprayed at the stages of wheat heading, blooming and filling, the composition not only has a synergistic effect for the prevention and control of barley scab and wheat scab, but also has the effect of decreasing the DON toxin contamination level, increasing thousand kernel weight and controlling powdery mildew, rust and leaf blight.

Beneficial Effect

The beneficial effect of the present invention is that compared with conventional fungicides, the fungicide composition of the present invention has the following advantages: (1) compared with the application of the single agents, the composition has an obvious synergistic effect when used for preventing and controlling *fusarium* head blight, and can remarkably enhance the effect of preventing and controlling head blight, increasing the ability of the human being in preventing and controlling head blight of triticeae crops; (2) the contamination level of DON toxin in grain can be remarkably decreased; (3) dosage, cost, environmental pollution and pesticide residue can be reduced; (4) the pressure of fungicide choice is decreased, the resistance of pathogenic fungi of wheat to metconazole can be retarded, and *fusarium* head blight which generates resistance to carbendazim can be prevented and controlled; (5) the persistent period of jinggangmycin is prolonged, the frequency of application is decreased, the powdery mildew, rust, leaf blight and sheath blight of triticeae can also be controlled, and the labor cost of pesticide application is reduced; (6) jinggangmycin is a pollution-free microbial pesticide with high selectivity, and by being mixed with metconazole, greatly reduces the dosage of the chemical pesticide, and the composition is environment-friendly.

DETAILED DESCRIPTION OF THE INVENTION

The present invention will be better understood through the following embodiments.

Embodiment 1: Experiment on 42 Percent of Jinggangmycin and Metconazole Composition Suspending Agent for Preventing and Controlling Wheat Diseases Time and Place of Experiment: April, 2015, Jiangsu Xinyang Farm Experimental Material: wheat, variety: Huaimai 33

Experimental Method:

Sample Preparation Method: Raw metconazole and raw jinggangmycin were mixed according to weight ratios of 1:20, 1:6, 5:16, 5:2 and 6:1, and according to the method of the research V described in the specification of the present application, 42 percent of experimental composition suspending agent samples with different ratios were obtained by processing. 25 mL of composition preparation, 50 mL of composition preparation and 100 mL of composition preparation were used per mu. Each composition preparation was mixed with water and sprayed at the initial stage of wheat blooming, and was sprayed for the second time 5 days later, and the amount of sprayed water per mu was 50 kg. Meanwhile, a corresponding dose of single wettable powder and spraying clean water were used as controls, carbendazim served as a control agent, each treatment was repeated two times, and the area of each plot was 100 square meters.

According to a corresponding method specified by Guidelines for the Field Efficacy Trials of Fungicides, the occurrences of wheat scab, powdery mildew, rust and leaf blight were investigated at the stage of milky ripeness, disease indexes, prevention and control effects, synergistic effects on head blight and effects in controlling toxin contamination were calculated, and results are listed in Table 11.

TABLE 11

Effect of 42 Percent of Jinggangmycin and Metconazole Composition Suspending Agent in Preventing and Controlling Wheat Diseases

| Serial Number | Treating Dosage (g ai. agent/mu) Jinggangmycin | Metconazole | Disease Index Prevention Effect % Head Blight | Leaf Blight | Powdery Mildew | Rust | Theoretical Prevention Effect of Mixed Agent on Head Blight % | Synergistic Coefficient | Grain Toxin Content (mg of DON/ Kg of grain) | Rate of Decrease in Toxin Content in Grains (%) |
|---|---|---|---|---|---|---|---|---|---|---|
| 1 | 1 | 20 | 89.8 | 87.4 | 92.6 | 100 | 75.1 | 120 | 0.28 | 95.7 |
| 2 | 0.5 | 10 | 88.4 | 85.1 | 82.3 | 85.4 | 70.1 | 126 | 0.36 | 94.4 |
| 3 | 3 | 18 | 90.1 | 84.6 | 87.2 | 91.5 | 74.9 | 120 | 0.30 | 95.4 |
| 4 | 1.5 | 9 | 85.6 | 80.3 | 80.5 | 88.4 | 67.2 | 127 | 0.41 | 93.7 |
| 5 | 5 | 16 | 92.3 | 81.0 | 85.6 | 90.3 | 74.6 | 124 | 0.26 | 96.0 |
| 6 | 2.5 | 8 | 88.2 | 79.6 | 78.7 | 85.8 | 65.1 | 135 | 0.44 | 93.2 |
| 7 | 15 | 6 | 89.1 | 80.2 | 73.4 | 82.8 | 65.8 | 135 | 0.43 | 93.3 |
| 8 | 7.5 | 3 | 64.2 | 65.6 | 64.4 | 75.9 | 40.4 | 162 | 0.78 | 87.9 |
| 9 | 36 | 6 | 88.3 | 83.6 | 74.3 | 88.2 | 69.1 | 128 | 0.48 | 92.6 |
| 10 | 18 | 3 | 73.8 | 73.5 | 56.9 | 72.6 | 49.0 | 151 | 0.62 | 90.4 |
| 11 | 36 | / | 31.6 | 5.8 | 8.5 | 7.6 | / | / | 2.61 | 59.6 |
| 12 | 18 | / | 28.9 | 5.0 | 7.8 | 7.2 | / | / | 2.86 | 55.7 |
| 13 | 15 | / | 24.3 | 4.6 | 7.6 | 7.2 | / | / | 2.94 | 54.5 |
| 14 | 7.5 | / | 16.9 | 0 | 0 | 0 | / | / | 3.42 | 47.1 |
| 15 | 5 | / | 5.2 | 0 | 0 | 0 | / | / | 3.86 | 40.2 |
| 16 | 2.5 | / | 0 | 0 | 0 | 0 | / | / | 3.92 | 39.3 |
| 17 | 3 | / | 0 | 0 | 0 | 0 | / | / | 3.96 | 38.7 |
| 18 | 1.5 | / | 0 | 0 | 0 | 0 | / | / | 4.82 | 25.4 |
| 19 | 1 | / | 0 | 0 | 0 | 0 | / | / | 5.80 | 10.2 |
| 20 | 0.5 | / | 0 | 0 | 0 | 0 | / | / | 5.86 | 9.3 |
| 21 | / | 20 | 75.1 | 80.5 | 80.1 | 91.2 | / | / | 1.11 | 82.8 |
| 22 | / | 18 | 74.9 | 80.2 | 74.6 | 88.4 | / | / | 0.99 | 84.7 |
| 23 | / | 16 | 73.2 | 79.6 | 71.4 | 85.6 | / | / | 1.08 | 83.3 |
| 24 | / | 10 | 70.1 | 75.3 | 63.4 | 82.1 | / | / | 1.34 | 79.3 |
| 25 | / | 9 | 67.2 | 75.0 | 60.8 | 82.4 | / | / | 1.56 | 75.9 |
| 26 | / | 8 | 65.1 | 74.3 | 58.6 | 79.4 | / | / | 1.61 | 75.1 |
| 27 | / | 6 | 54.8 | 70.2 | 51.8 | 72.6 | / | / | 1.89 | 70.7 |
| 28 | / | 3 | 28.3 | 28.1 | 26.4 | 30.2 | / | / | 3.22 | 50.2 |
| 29 | Carbendazim 50 g a.i. | | 49.04 | / | / | / | / | / | 4.35 | 32.7 |
| 30 | Blank Control Disease Index | | 35.2 | 14.3 | 22.7 | 20.1 | / | / | 6.46 | / |

The above-mentioned field application results indicate that 0.5 g to 36 g of jinggangmycin and 3 g to 20 g of metconazole have a good wheat disease prevention and control effect when used. The synergistic coefficient for the prevention and control of head blight is 120 to 162, so the synergistic effect is prominent. However, when 3 g to 15 g of jinggangmycin and 3 g to 16 g of metconazole are applied per mu, the toxin contamination level is remarkably decreased, the synergistic effect is extremely obvious, the effect in preventing and controlling head blight is not less than 85 percent, and furthermore, powdery mildew, rust and leaf blight of wheat can also be effectively controlled. When 18 g to 36 g of jinggangmycin and 16 g to 20 g of metconazole are applied per mu, the disease prevention and control effect is not increased notably. These results also indicate that when 0.5 g to 36 g of jinggangmycin and 3 g to 20 g of metconazole are adopted per mu, the DON toxin content in grains is reduced by not less than 90 percent in comparison with that in the control, and in comparison with the toxin reduction effect of jinggangmycin or metconazole used for treatment alone, the toxin reduction effect is also extremely outstanding.

and 64 percent of experimental wettable powder sample was prepared according to the method of the research VII described in the specification of the present application. The composition wettable powder containing 4 g to 20 g of the active jinggangmycin ingredient and the active metconazole ingredient was respectively used per mu. The composition wettable powder was mixed with water and sprayed on Yangmai 4 at the initial stage of wheat blooming, and was sprayed for the second time 5 days later, and the amount of sprayed water per mu was 45 kg. A dose of 20 percent of single-agent wettable powder used in mixture and spraying clean water were used as controls, and 60 g of 50 percent of polyketone wettable powder per mu was adopted as a control agent. Each treatment was repeated three times, and the area of each plot was 50 square meters. According to a corresponding method specified by Guidelines for the Field Efficacy Trials of Fungicides, the occurrences of wheat scab, powdery mildew, rust and leaf blight were investigated at the stage of milky ripeness, and disease indexes and prevention and control effects were calculated. The result can be seen in Table 12.

TABLE 12

Effect of 64 Percent of Jinggangmycin and Metconazole Composition Wettable Powder in Preventing and Controlling Wheat Disease

| Preparation | | Active Ingredient Dosage | | Disease Index Prevention Effect % | | | | Theoretical Prevention Effect | | Thousand Kernel |
|---|---|---|---|---|---|---|---|---|---|---|
| Serial Number | Dosage (g/mu) | (g ai. agent/mu) | | Head Blight | Leaf Blight | Powdery Mildew | Rust | on Head Blight % | Synergistic Coefficient | Weight (g) |
| | | Jinggangmycin | Metconazole | | | | | | | |
| 1 | 12.5 | 4 | 4 | 85.2 | 79.4 | 78.8 | 75.3 | 52.0 | 164 | 42.8 |
| 2 | 25 | 8 | 8 | 96.3 | 85.2 | 87.3 | 84.4 | 71.9 | 134 | 43.2 |
| 3 | 50 | 16 | 16 | 96.6 | 91.8 | 99.2 | 98.6 | 78.5 | 123 | 43.6 |
| 4 | 62.5 | 20 | 20 | 97.5 | 92.4 | 100 | 100 | 85.2 | 114 | 43.6 |
| 5 | 100 | 20 | / | 32.0 | 8.6 | 12.6 | 6.8 | / | / | 39.2 |
| 6 | 80 | 16 | / | 25.4 | 8.8 | 11.9 | 6.5 | / | / | 41.1 |
| 7 | 40 | 8 | / | 14.7 | 5.8 | 0 | 0 | / | / | 39.8 |
| 8 | 20 | 4 | / | 0 | 0 | 0 | 0 | / | / | 39.5 |
| 9 | 100 | / | 20 | 78.2 | 72.8 | 83.2 | 84.4 | / | / | 42.8 |
| 10 | 80 | / | 16 | 71.2 | 70.6 | 75.4 | 77.3 | / | / | 41.8 |
| 11 | 40 | / | 8 | 67.1 | 68.3 | 69.2 | 70.6 | / | / | 42.0 |
| 12 | 20 | / | 4 | 52.0 | 50.8 | 60.6 | 63.8 | / | / | 39.2 |
| 13 | 60 | Polyketone 30 | | 54.6 | 65.2 | 75.4 | 76.8 | / | / | 39.3 |
| 14 | Blank Control Disease Index | | | 35.6 | 14.8 | 25.1 | 20.6 | / | / | 37.2 |

Embodiment 2: Effect of 64 Percent of Jinggangmycin and Metconazole Composition Wettable Powder in Preventing and Controlling Wheat Diseases Time and Place of Experiment: April, 2015, Jiangsu Yanjiang Institute of Agricultural Sciences (Rugao)

Experimental Material: wheat cultivar: Yangmai 4

Experimental Method: Raw metconazole and raw jinggangmycin were mixed according to a weight ratio of 1:1, The above-mentioned field application results indicate that the compositions in which the effective contents of jinggangmycin and metconazole according to the weight ratio of 1:1 are 4 g to 20 g each has a good prevention and control effect on wheat scab, leaf blight, powdery mildew and rust when used per mu, but the effect is better when 4 g to 8 g of active jinggangmycin ingredient and 4 g to 8 g of active metconazole ingredient are used. The composition for treatment can notably increase thousand kernel weight, and the yield-increasing effect is obvious.

Embodiment 3: Effect of 20 Percent of Jinggangmycin and Metconazole Composition Wettable Powder in Preventing and Controlling Wheat Diseases and Reducing Toxin Contamination Time and Place of Experiment: April, 2015, Jiangsu Yanjiang Institute of Agricultural Sciences (Rugao), arranging the experiment in the same plots in embodiment 2.

Experimental Material: wheat cultivar: Yangmai 4

Experimental Method: After raw metconazole and raw jinggangmycin were mixed according to a weight ratio of 1:1, the mixture was added with 10 percent by weight of kaolin carrier, 2 percent by weight of sodium lignin sulfonate adjuvant, 2 percent by weight of carboxymethylcellulose, 1 percent by weight of alkylphenol polyoxyethylene ether phosphate and 2 percent by weight of polyvinyl alcohol and, finally, added with light calcium carbonate carries to 100 percent, and the mixture was milled by a sand mill and screened by a 300-mesh screen. An experimental composition wettable powder sample, the content of which was 20 percent, was prepared. The composition wettable powders containing 20 g, 15 g and 6 g of the active jinggangmycin ingredient and the active metconazole ingredient were respectively used per mu. The composition wettable powder was mixed with water and sprayed on Yangmai 4 at the initial stage of wheat blooming, and was sprayed for the second time 5 days later, and the amount of sprayed water per mu was 45 kg. A dose of 20 percent of single-agent wettable powder used in mixture and spraying clean water were used as controls, and 60 g of 50 percent of polyketone wettable powder per mu was adopted as a control agent. Each treatment was repeated three times, and the area of each plot was 50 square meters. According to a corresponding method specified by Guidelines for the Field Efficacy Trials of Fungicides, the occurrences of wheat scab, powdery mildew, rust and leaf blight were investigated at the stage of milky ripeness, and disease indexes and prevention and control effects were calculated. Experimental results are listed in Table 13.

The above-mentioned experimental results indicate that the jinggangmycin and metconazole composition has an outstanding synergistic effect for the prevention and control of head blight and an outstanding yield-increasing effect. Such effects are related to a used dosage, but have no significant relationship with the content and adjuvant of the processed preparation.

Embodiment 4: Effect of 30 Percent of Jinggangmycin and Metconazole Composition Water-Dispersible Granule in Preventing and Controlling Wheat Diseases and Reducing Toxin Contamination Time and Place of Experiment: April, 2015, Jiangsu White Horse Lake Farm Experimental Material: wheat cultivar: Huamai 4

Experimental Method: 30 percent of composition water-dispersible granule was obtained by processing according to a weight ratio of 5:1 of jinggangmycin to metconazole. A processing method was as follows: 39.1 parts by weight of 64 percent of jinggangmycin (25 parts of active ingredient), 5.2 parts by weight of 96.2 percent of raw metconazole (5 parts of active ingredient), 30 parts by weight of ammonium sulfate, 17.2 parts by weight of light calcium carbonate, 2.5 parts by weight of alkylphenol ethoxylates, 2.5 parts by weight of sodium dodecyl benzene sulfonate and 3.5 parts by weight of polyoxyethylene fatty acid were ground, screened and pelletized.

200 g, 100 g, 50 g and 30 g of composition preparations were used per mu, mixed with water and sprayed at the initial stage of wheat blooming and sprayed for the second time 5 days later, and the amount of sprayed water per mu was 50 kg. 100 g of 20 percent of single wettable powder per mu and spraying clean water were used as controls, each treatment was repeated three times, and the area of each plot was 50 square meters. According to a corresponding method specified by Guidelines for the Field Efficacy Trials of Fungicides, the occurrences of wheat scab, powdery mildew, rust and leaf blight were investigated at the stage of milky ripeness, and disease indexes and prevention and control effects were calculated. Experimental results are listed in Table 14.

TABLE 13

Effect of 20 Percent of Jinggangmycin and Metconazole Composition Wettable Powder in Preventing and Controlling Wheat Diseases

| Serial Number | Preparation Dosage (g/mu) | Active Ingredient Dosage (g ai. agent/mu) | | Disease Index Prevention Effect % | | | | Theoretical Prevention Effect on Head Blight % | Synergistic Coefficient | Thousand Kernel Weight (g) |
|---|---|---|---|---|---|---|---|---|---|---|
| | | Jinggangmycin | Metconazole | Head Blight | Leaf Blight | Powdery Mildew | Rust | | | |
| 1 | 30 | 3.0 | 3.0 | 76.2 | 70.4 | 68.8 | 73.3 | 39.1 | 195 | 41.2 |
| 2 | 75 | 7.5 | 7.5 | 93.8 | 83.3 | 80.4 | 83.8 | 75.1 | 125 | 42.6 |
| 3 | 100 | 10 | 10 | 95.4 | 86.6 | 90.1 | 94.2 | 83.5 | 114 | 44.1 |
| 5 | 50 | 10 | / | 32.4 | 8.6 | 12.6 | 6.8 | / | / | 39.6 |
| 6 | 37.5 | 7.5 | / | 24.2 | 8.8 | 11.9 | 6.5 | / | / | 39.0 |
| 7 | 15 | 3 | / | 0 | 5.8 | 0 | 0 | / | / | 37.9 |
| 8 | 50 | / | 10 | 75.6 | 72.8 | 83.2 | 84.4 | / | / | 43.2 |
| 9 | 37.5 | / | 7.5 | 67.1 | 70.6 | 75.4 | 77.3 | / | / | 42.6 |
| 10 | 15 | / | 3 | 39.1 | 68.3 | 69.2 | 70.6 | / | / | 39.8 |
| 11 | 60 | Polyketone 30 | | 54.6 | 65.2 | 75.4 | 76.8 | / | / | 39.3 |
| 12 | Blank Control Disease Index | | | 35.6 | 14.8 | 25.1 | 20.6 | / | / | 37.2 |

TABLE 14

Effect of 60 Percent of Jinggangmycin and Metconazole Composition Water-dispersible Granule in Preventing and Controlling Wheat Diseases

| Serial Number | Preparation Dosage (g/mu) | Active Ingredient Dosage (g ai. agent/mu) | | Disease Index Prevention Effect % | | | |
|---|---|---|---|---|---|---|---|
| | | Jinggangmycin | Metconazole | Head Blight | Leaf Blight | Powdery Mildew | Rust |
| 1 | 200 | 100 | 20 | 89.2 | 84.4 | 96.8 | 95.2 |
| 2 | 100 | 50 | 10 | 88.3 | 85.2 | 91.4 | 92.1 |
| 3 | 50 | 25 | 5 | 88.6 | 84.8 | 86.7.2 | 83.3 |
| 4 | 30 | 15 | 3 | 85.1 | 68.2 | 72.9 | 70.1 |
| 5 | 100 | 20 | 0 | 40.2 | 7.8 | 10.6 | 6.5 |
| 6 | 100 | 0 | 20 | 83.4 | 84.6 | 98.2 | 100 |
| 7 | Blank Control Disease Index | | | 25.9 | 23.4 | 29.7 | 24.0 |

The above-mentioned field application effect indicates that when sprayed according to 18 g to 120 g of active ingredients of the composition water-dispersible granule with 5 parts of jinggangmycin and 1 part of metconazole, the composition water-dispersible granule has a good prevention and control effect on wheat scab, powdery mildew, rust and leaf blight, and in particular, when 18 g to 60 g of active ingredients of the composition is sprayed per mu, the cost performance is best.

Embodiment 5: Effect of 32 Percent of Jinggangmycin and Metconazole Composition Emulsion in Water in Preventing and Controlling Wheat Diseases Time and Place of Experiment: April, 2015, Jiangsu White Horse Lake Farm Experimental Material: wheat cultivar: Huamai 4

Experimental Method: A preparation method for 32 percent of composition emulsion in water was as follows: raw metconazole was prepared into a suspending agent, and the suspending agent was added with an ethyleneoxide-propyleneoxide block polymer non-ionic emulsifier and stirred into the uniform oil phase; and in addition, a jinggangmycin aqueous solution, an ethylene glycol antifreezing agent and 1 percent of benzoic acid were mixed into the aqueous phase. Under high-speed stirring, the aqueous phase was gradually added into the oil phase, so that 32 percent of oil-in-water emulsion in water in which the ratio of jinggangmycin to metconazole was 1:3 was prepared.

100 mL, 50 mL, 25 mL and 12.5 mL of composition emulsions in water were used per mu, each composition emulsion in water was mixed with water and sprayed at the initial stage of wheat blooming and sprayed for the second time 5 days later, and the amount of sprayed water per mu was 50 kg. 100 g of 20 percent of single wettable powder per mu and spraying clean water were used as controls, each treatment was repeated three times, and the area of each plot was 50 square meters. According to a corresponding method specified by Guidelines for the Field Efficacy Trials of Fungicides, the occurrences of wheat scab, powdery mildew, rust and leaf blight were investigated at the stage of milky ripeness, and disease indexes and prevention and control effects were calculated. Experimental results are listed in Table 15.

TABLE 15

Effect of 32 Percent of Jinggangmycin and Metconazole Composition Emulsion in water in Preventing and Controlling Wheat Diseases

| Serial Number | Preparation Dosage (mL/mu) | Active Ingredient Dosage (g ai. agent/mu) | | Disease Index Prevention Effect % | | | |
|---|---|---|---|---|---|---|---|
| | | Jinggangmycin | Metconazole | Head Blight | Leaf Blight | Powdery Mildew | Rust |
| 1 | 100 | 8 | 24 | 94.6 | 88.4 | 99.8 | 97.2 |
| 2 | 50 | 4 | 12 | 91.3 | 87.5 | 95.6 | 93.7 |
| 3 | 25 | 2 | 6 | 82.6 | 80.8 | 81.7 | 80.2 |
| 4 | 12.5 | 1 | 3 | 60.2 | 61.4 | 62.3 | 62.2 |
| 5 | 100 | 20 | 0 | 34.2 | 7.8 | 10.6 | 6.5 |
| 6 | 100 | 0 | 20 | 82.4 | 80.6 | 78.2 | 85.0 |
| 7 | Blank Control Disease Index | | | 35.9 | 23.4 | 29.7 | 24.6 |

The above-mentioned field application results indicate that when 8 g to 32 g of active ingredients of the jinggangmycin and metconazole composition is used per mu, the prevention and control effect on wheat scab, powdery mildew, rust and leaf blight is good, and when 4 g of active ingredients of the composition is used per mu, the effect in preventing and controlling these wheat diseases is also outstanding.

Embodiment 6: Effect of 45 Percent of Jinggangmycin and Metconazole Wettable Powder in Preventing and Controlling Wheat Diseases and Reducing Toxin Contamination Time and Place of Experiment: April, 2015, Jiangsu Yanjiang Institute of Agricultural Sciences (Rugao)

adopted as control agents for treatment, spraying clean water was adopted as a blank control, each treatment is repeated three times, and the area of each plot was 50 square meters. According to a corresponding method specified by Guidelines for the Field Efficacy Trials of Fungicides, the occurrences of wheat scab and powdery mildew were investigated at the stage of milky ripeness, and disease indexes and prevention and control effects were calculated.

During harvest, two hundred ears were sampled in total every five treated points, and after being threshed, the samples were sent to Nanjing Agricultural University for toxin content assay. The toxin assay method is the same as that mentioned above. Experimental results are listed in Table 16.

TABLE 16

Effect of 45 Percent of Jinggangmycin and Metconazole Composition Wettable Powder in Preventing and Controlling Wheat Diseases

| | Preparation Dosage | Active Ingredient Dosage (g ai. agent/mu) | | Disease Index Prevention Effect % | | Synergistic Effect | | | | | |
|---|---|---|---|---|---|---|---|---|---|---|---|
| | | | | | | Theoretical Prevention Effect on | Theoretical Prevention Effect on | Synergistic Coefficient on | Synergistic Coefficient on | Grain Toxin | Toxin |
| Serial Number | Dosage (g/mu) | Jinggangmycin | Metconazole | Head Blight | Powdery Mildew | Head Blight | Powdery Mildew | Head Blight | Powdery Mildew | Content mg of DON/kg of grain | Reduction Percentage % |
| 1 | 50 | 15 | 7.5 | 94.6 | 90.8 | 70.8 | 70.8 | 134 | 128 | 0.22 | 95.1 |
| 2 | 40 | 12 | 6 | 89.3 | 85.6 | 57.2 | 63.2 | 156 | 135 | 0.34 | 92.5 |
| 3 | 30 | 9 | 4.5 | 82.6 | 84.7 | 54.3 | 51.1 | 152 | 166 | 0.66 | 85.4 |
| 4 | 20 | 6 | 3 | 70.2 | 66.3 | 33.9 | 46.1 | 207 | 144 | 1.28 | 71.7 |
| 5 | 75 | 15 | / | 34.2 | 8.6 | / | / | / | / | 2.86 | 36.7 |
| 6 | 60 | 12 | / | 10.2 | 6.6 | / | / | / | / | 3.82 | 15.5 |
| 7 | 45 | 9 | / | 9.4 | 3.0 | / | / | / | / | 4.02 | 11.1 |
| 8 | 30 | 6 | / | 7.4 | 1.8 | / | / | / | / | 4.14 | 8.4 |
| 9 | 37.5 | / | 7.5 | 55.6 | 68.8 | / | / | / | / | 2.01 | 55.5 |
| 10 | 30 | / | 6 | 52.3 | 60.6 | / | / | / | / | 2.17 | 52.0 |
| 11 | 22.5 | / | 4.5 | 49.6 | 58.6 | / | / | / | / | 2.06 | 54.4 |
| 12 | 15 | / | 3 | 28.6 | 45.1 | / | / | / | / | 3.12 | 31.0 |
| 13 | | 80 g of 50% of Carbendazim Wettable Powder | | 64.6 | 62.8 | / | / | / | / | 2.95 | 34.7 |
| 14 | | Blank Control Disease Index | | 21.8 | 15.2 | / | / | / | / | 4.52 | / |

Experimental Material: wheat cultivar: Yangmai 4

Experimental Method: 45 percent of experimental wettable powder sample in which the weight ratio of jinggangmycin to metconazole was 2:1 was prepared according to the method of the research VII described in the specification of the present application, and Jiangsu Yanjiang Institute of Agricultural Sciences was commissioned to carry out a field experiment. 50 g, 40 g, 30 g and 20 g of composition wettable powder preparations were used per mu respectively. Each composition wettable powder preparation was mixed with water and sprayed at the initial stage of wheat blooming, and was sprayed for the second time 5 days later, and the amount of sprayed water per mu was 50 kg. 20 percent of single jinggangmycin and metconazole wettable powder was adopted, doses of single agents in the used mixed agent and 40 g of active carbendazim ingredient were It can be seen from the experimental results of the above-mentioned field application embodiments 1-6 that based on the discovery that jinggangmycin can inhibit the pathogenic factor DON toxin biosynthesis of the head blight fungi, the jinggangmycin and metconazole composition has an outstanding synergistic effect for the prevention and control of wheat scab when adopted to treat wheat seeds and be sprayed in fields. Moreover, the prevention and control effect on powdery mildew, rust, leaf blight and sheath blight of triticeae crops is also ideal. In addition, after the inventor adopted some of the combined jinggangmycin and metconazole compositions to carry out experimental demonstration in Jiangsu Yanjiang Institute of Agricultural Sciences, Jiangsu Xinyang Farm and White Horse Lake Farm for three years, the jinggangmycin and metconazole compositions all showed an excellent prevention effect on barley scab and wheat scab, and could also effectively control powdery mildew, leaf blight and rust. The present invention not only solves the major problem confronting China at present that the wheat scab fungi are hard to prevent and control due to carbendazim resistance, but also can overcome the food safety problem caused by wheat contaminated by DON toxin. Compared with conventional fungicides in the prior art, the jinggangmycin and metconazole composition of the present invention can greatly reduce the contamination of grains by the DON toxin of fusaria, and can also greatly reduce chemical pesticide dosage and application cost because of the synergistic effect, and thereby the jinggangmycin and metconazole composition has a good application prospect in reducing environmental pollution, controlling pesticide-resistant fungal diseases of triticeae and guaranteeing food safety.

What is claimed is:

1. A method for using a pesticide composition for preventing and controlling *fusarium* head blight comprising a step of administering the pesticide composition to grain crops infected or to be infected by fungi of *Fusarium*, wherein the pesticide composition comprises 1-500 parts of jinggangmycin: 1-20 parts of metconazole by weight.

2. The method according to claim 1, wherein the pesticide composition comprises 30-100 parts of jinggangmycin: 3-18 parts of metconazole by weight.

3. The method according to claim 1, wherein the pesticide composition comprises 50-65 parts of jinggangmycin: 6-18 parts of metconazole by weight.

4. The method according to claim 1, wherein the pesticide composition comprises a carrier and/or an adjuvant acceptable in pesticides, and a mixture of jinggangmycin and metconazole is 0.1 to 90.0% of the total weight of the pesticide composition.

5. The method according to claim 4, the mixture of jinggangmycin and metconazole is 10 to 75.0% of the total weight of the pesticide composition.

6. The method according to claim 4, the mixture of jinggangmycin and metconazole is 26.0 to 58.0% of the total weight of the pesticide composition.

7. The method according to claim 4, wherein the form of pesticide composition is a suspending agent, an emulsion in water, a microemulsion, a wettable powder or a water-dispersible granule.

8. The method according to claim 4, the carrier is one or more selecting from a group consisting of water, attapulgite, kaolin and light calcium carbonate.

9. The method according to claim 4, the adjuvant is selecting from a group consisting of ethanol, methanol, ethylene glycol, propylene glycol, NNO-1, NNO-7, xanthan gum, polyethylene glycol, glycerol, nekal, sodium dodecyl sulfate, sodium dodecyl benzene sulfonate, ammonium sulfate, alkylphenol ethoxylates, alkylphenol polyoxyethylene ether phosphate, polyoxyethylene fatty acid, benzoic acid, sodium lignin sulfonate, carboxymethylcellulose and polyvinyl alcohol.

10. The method according to claim 1, wherein the *fusarium* head blight is wheat scab and barley scab of triticeae crops caused by *fusarium* pathogenic fungi (*Fusarium* spp.).

11. The method according to claim 10, wherein the wheat scab and barley scab are bud rot, seedling blight, ear rot or ear blight.

* * * * *